(12) United States Patent
Shin et al.

(10) Patent No.: US 11,302,875 B2
(45) Date of Patent: Apr. 12, 2022

(54) ORGANIC ELECTROLUMINESCENCE DEVICE

(71) Applicant: LG DISPLAY CO., LTD., Seoul (KR)

(72) Inventors: Jicheol Shin, Seoul (KR); Seonkeun Yoo, Gunpo-si (KR); Sangbeom Kim, Paju-si (KR); Soyoung Jang, Seoul (KR); Heejun Park, Paju-si (KR)

(73) Assignee: LG DISPLAY CO., LTD., Seoul (KR)

( * ) Notice: Subject to any disclaimer, the term of this patent is extended or adjusted under 35 U.S.C. 154(b) by 366 days.

(21) Appl. No.: 16/563,025

(22) Filed: Sep. 6, 2019

(65) Prior Publication Data
US 2020/0106025 A1 Apr. 2, 2020

(30) Foreign Application Priority Data

Oct. 1, 2018 (KR) .................... 10-2018-0117127

(51) Int. Cl.
*H01L 51/50* (2006.01)
*H01L 51/00* (2006.01)
*H01L 51/52* (2006.01)

(52) U.S. Cl.
CPC ...... *H01L 51/0072* (2013.01); *H01L 51/0051* (2013.01); *H01L 51/0067* (2013.01); *H01L 51/506* (2013.01); *H01L 51/5068* (2013.01); *H01L 51/5084* (2013.01); *H01L 51/5206* (2013.01); *H01L 51/5221* (2013.01)

(58) Field of Classification Search
None
See application file for complete search history.

(56) References Cited

U.S. PATENT DOCUMENTS

| 10,096,782 | B2 | 10/2018 | Yoo et al. |
| 10,879,472 | B2 | 12/2020 | Yoo et al. |
| 2015/0090984 | A1 | 4/2015 | Kang et al. |
| 2018/0166647 | A1 | 6/2018 | Shin et al. |
| 2019/0181354 | A1* | 6/2019 | Shin ................... H01L 51/0072 |

FOREIGN PATENT DOCUMENTS

| CN | 105321984 A | 2/2016 |
| CN | 107556307 A | 1/2018 |
| EP | 3010056 A1 | 4/2016 |
| EP | 3333921 A1 | 6/2018 |
| KR | 10-2015-0039631 A | 4/2015 |
| KR | 10-2018-0067321 A | 6/2018 |

\* cited by examiner

*Primary Examiner* — Gregory D Clark
(74) *Attorney, Agent, or Firm* — Birch, Stewart, Kolasch & Birch, LLP

(57) ABSTRACT

Disclosed is an organic electroluminescence device including an anode, a cathode, at least two light-emission sub-stacks and a charge generation layer. The charge generation layer is located between the light-emission sub-stacks, and the charge generation layer includes a stack of a n-type charge generation layer and a p-type charge generation layer. The n-type charge generation layer includes a Compound of Formula 1 and a Compound of Formula 2. The present organic electroluminescence device improves injection and transport properties of electrons to lower driving voltage of the device, improves efficiency and lifespan of the device, and has excellent thermal/electrical stability for long driving duration of the device.

21 Claims, 18 Drawing Sheets

ORGANIC ELECTROLUMINESCENCE DEVICE

CROSS-REFERENCE TO RELATED APPLICATIONS

This application claims the priority of Korean Patent Application No. 10-2018-0117127 filed on Oct. 1, 2018, in the Korean Intellectual Property Office, the disclosure of which is hereby incorporated by reference in its entirety.

BACKGROUND

1. Technical Field

The present disclosure relates to an organic electroluminescence device.

2. Description of the Related Art

As a size of a display device has been increased, there has been a growing interest in a flat display device with a small occupancy. A technique of an organic light-emission display device including an organic electroluminescence device or an organic light-emission diode (OLED) as one of such flat display devices has been rapidly developed.

In the organic light-emitting diode (OLED), when charges are injected into a light-emission layer formed between an anode and a cathode, paired electrons and holes form excitons. Then, light emission occurs when the exciton falls to a ground state. In addition, the organic light emitting diode is driven at a lower voltage than that of a conventional display device, has relatively low power consumption, and has excellent color rendering and is applicable to a flexible substrate for various applications.

SUMMARY

A purpose of the present disclosure is to provide an organic electroluminescence device including a mixed n-type charge generation layer which improves injection and transport properties of electrons to lower a driving voltage, and to improve the efficiency and lifespan of the device, and has excellent thermal/electrical stability for long driving duration of the device.

The purposes of the present disclosure are not limited to the above-mentioned purposes. Other purposes and advantages of the present disclosure, as not mentioned above, may be understood from the following descriptions and more clearly understood from the embodiments of the present disclosure. Further, it will be readily appreciated that the purposes and advantages of the present disclosure may be realized by features and combinations thereof as disclosed in the claims.

In one aspect of the present disclosure, an organic electroluminescence device according to the present disclosure includes: at least two light-emission sub-stacks located between an anode and a cathode, wherein each of the at least two light-emission sub-stacks includes at least one light-emission layer; and a charge generation layer located between the two light-emission sub-stacks. The charge generation layer includes a stack of a n-type charge generation layer and a p-type charge generation layer. The n-type charge generation layer faces the anode, while the p-type charge generation layer faces the cathode. The n-type charge generation layer contains a compound represented by Chemical Formula 1 and a compound represented by Chemical Formula 2:

[Chemical Formula 1]

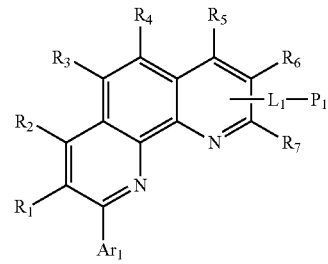

In the Chemical Formula 1, each of $R_1$ to $R_7$ independently represents any one selected from the group consisting of hydrogen, a C1 to C20 monovalent aliphatic chain group, and a C3 to C30 monovalent aliphatic ring group, $L_1$ represents any one selected from the group consisting of a single bond, a substituted or unsubstituted C5 to C60 arylene group, a substituted or unsubstituted C4 to C60 heteroarylene group, and combinations thereof, $Ar_1$ represents a substituted or unsubstituted C5 to C60 aryl group, $P_1$ represents a substituted or unsubstituted C5 to C60 aryl group, wherein the aryl group defined as $P_1$ unsubstituted or substituted with any one selected from the group consisting of a C1 to C20 aliphatic chain linked to an aromatic ring, a C3 to C30 aliphatic ring linked to an aromatic ring, and combinations thereof.

[Chemical Formula 2]

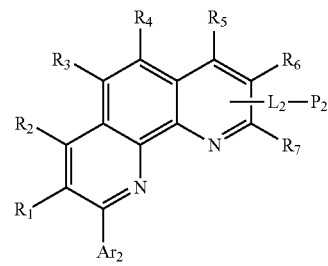

In the Chemical Formula 2, each of $R_1$ to $R_7$ independently represents any one selected from the group consisting of hydrogen, a C1 to C20 monovalent aliphatic chain group and a C3 to C30 monovalent aliphatic ring group, $L_2$ represents any one selected from the group consisting of a single bond, a substituted or unsubstituted C5 to C60 arylene group, a substituted or unsubstituted C4 to C60 heteroarylene group, and combinations thereof, $Ar_2$ represents a substituted or unsubstituted C5 to C60 aryl group or a substituted or unsubstituted C4 to C60 heteroaryl group, $P_2$ represents a substituted or unsubstituted C4 to C60 heteroaryl group, wherein the heteroaryl group defined as $P_2$ unsubstituted or substituted with any one selected from the group consisting of a C1 to C20 aliphatic chain linked to an aromatic heterocyclic ring, a C3 to C30 aliphatic ring linked to an aromatic heterocyclic ring, and combinations thereof.

The n-type charge generation layer of the organic electroluminescence device according to the present disclosure includes a mixture of the compound represented by the Chemical Formula 1 and a compound represented by the Chemical Formula 2 as a host material. Thus, the n-type charge generation layer may improve the injection and migration characteristics of the electron to lower the driving voltage, and to improve the efficiency and lifespan of the device, and may have excellent thermal and electrical stability for high temperature and long deposition and long driving duration of the device.

In addition to the above effects, specific effects of the present disclosure are described below in conjunction with descriptions of specific details to implement the present disclosure.

BRIEF DESCRIPTION OF THE DRAWINGS

The present invention will become more fully understood from the detailed description given hereinbelow and the accompanying drawings, which are given by illustration only, and thus are not limitative of the present invention, and wherein.

DETAILED DESCRIPTION

Figure 1:
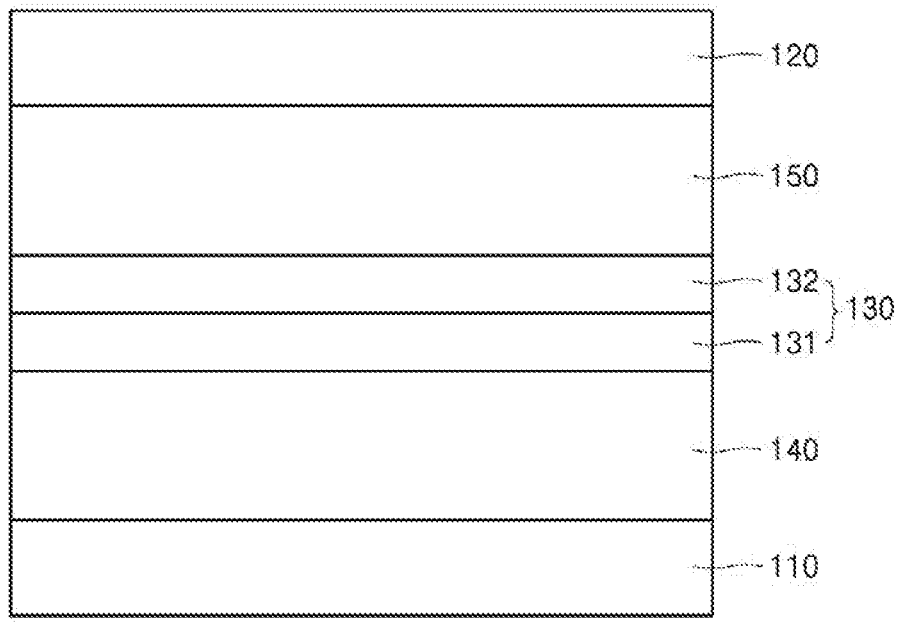
FIG. 1 is a cross-sectional view schematically illustrating an organic electroluminescence device according to an embodiment of the present disclosure.

For simplicity and clarity of illustration, elements in the figures are not necessarily drawn to scale. The same reference numbers in different figures denote the same or similar elements, and as such perform similar functionality. Furthermore, in the following detailed description of the present disclosure, numerous specific details are set forth in order to provide a thorough understanding of the present disclosure. However, it will be understood that the present disclosure may be practiced without these specific details. In other instances, well-known methods, procedures, components, and circuits have not been described in detail so as not to unnecessarily obscure aspects of the present disclosure.

Examples of various embodiments are illustrated and described further below. It will be understood that the description herein is not intended to limit the claims to the specific embodiments described. On the contrary, it is intended to cover alternatives, modifications, and equivalents as may be included within the spirit and scope of the present disclosure as defined by the appended claims.

The terminology used herein is for the purpose of describing particular embodiments only and is not intended to be limiting of the present disclosure. As used herein, the singular forms "a" and "an" are intended to include the plural forms as well, unless the context clearly indicates otherwise. It will be further understood that the terms "comprises", "comprising", "includes", and "including" when used in this specification, specify the presence of the stated features, integers, operations, elements, and/or components, but do not preclude the presence or addition of one or more other features, integers, operations, elements, components, and/or portions thereof. As used herein, the term "and/or" includes any and all combinations of one or more of the associated listed items. Expression such as "at least one of" when preceding a list of elements may modify the entire list of elements and may not modify the individual elements of the list.

It will be understood that, although the terms "first", "second", "third", and so on may be used herein to describe various elements, components, regions, layers and/or sections, these elements, components, regions, layers and/or sections should not be limited by these terms. These terms are used to distinguish one element, component, region, layer or section from another element, component, region, layer or section. Thus, a first element, component, region, layer or section described below could be termed a second element, component, region, layer or section, without departing from the spirit and scope of the present disclosure.

In addition, it will also be understood that when a first element or layer is referred to as being present "on" a second element or layer, the first element may be disposed directly on the second element or may be disposed indirectly on the second element with a third element or layer being disposed between the first and second elements or layers. It will be understood that when an element or layer is referred to as being "connected to", or "coupled to" another element or layer, it can be directly on, connected to, or coupled to the other element or layer, or one or more intervening elements or layers may be present. In addition, it will also be understood that when an element or layer is referred to as being "between" two elements or layers, it can be the only element or layer between the two elements or layers, or one or more intervening elements or layers may also be present.

Unless otherwise defined, all terms including technical and scientific terms used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

As used herein, a term "unsubstituted" means that a hydrogen atom is maintained. In this case, the hydrogen atom includes protium, deuterium and tritium. As used herein, a substituent associated with the term "substituted" may include any one selected from the group consisting of, for example, an alkyl group of 1 to 20 carbon atoms unsubstituted or substituted with halogen, an alkoxy group having 1 to 20 carbon atoms unsubstituted or substituted with halogen, halogen, a cyano group, a carboxy group, a carbonyl group, an amine group, an alkylamine group having 1 to 20 carbon atoms, a nitro group, a hydrazyl group, a sulfonic acid group, an alkylsilyl group having 1 to 20 carbon atoms, an alkoxysilyl group having 1 to 20 carbon atoms, a cycloalkylsilyl group having 3 to 30 carbon atoms, an arylsilyl group having 5 to 30 carbon atoms, an aryl group having 5 to 30 carbon atoms, a heteroaryl group having 4 to 30 carbon atoms, and a combination thereof. However, the present disclosure is not limited thereto.

As used herein, the term "hetero" as used in the terms "heteroaromatic ring", "heterocycloalkylene group", "heteroarylene group", "heteroarylalkylene group", "heterooxyarylene group", "heterocycloalkyl group", "heteroaryl group", "heteroarylalkyl group", "heterooxyaryl group", "heteroarylamine group", etc. means that one or more carbon atoms, for example, 1 to 5 carbon atoms among carbon atoms constituting the aromatic ring or alicyclic ring are substituted with at least one hetero atom selected from a group consisting of N, O, S and combinations thereof.

As used herein, the phase "combination thereof" as used in the definition of the substituent means that two or more substituents are bonded to each other via a linking group or two or more substituents are bonded to each other via condensation, unless otherwise defined.

Hereinafter, organic electroluminescence devices according to embodiments of the present disclosure will be described. In one implementation of the present disclosure, an organic electroluminescence device includes: at least two light-emission sub-stacks located between an anode and a cathode, wherein each of the at least two light-emission sub-stacks includes at least one light-emission layer; and a charge generation layer located between the two light-emission sub-stacks. The charge generation layer includes a stack of a n-type charge generation layer and a p-type charge generation layer. The n-type charge generation layer faces the anode, while the p-type charge generation layer faces the cathode. The n-type charge generation layer contains a compound represented by a following Chemical Formula 1 and a compound represented by a following Chemical Formula 2:

[Chemical Formula 1]

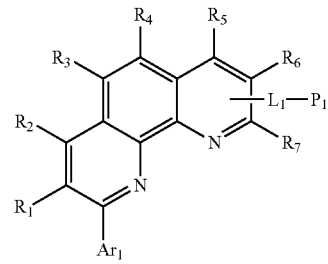

In the Chemical Formula 1, each of $R_1$ to $R_7$ independently represents any one selected from the group consisting of hydrogen, a C1 to C20 monovalent aliphatic chain group, and a C3 to C30 monovalent aliphatic ring group, $L_1$ represents any one selected from the group consisting of a single bond, a substituted or unsubstituted C5 to C60 arylene group, a substituted or unsubstituted C4 to C60 heteroarylene group, and combinations thereof, $Ar_1$ represents a substituted or unsubstituted C5 to C60 aryl group, $P_1$ represents a substituted or unsubstituted C5 to C60 aryl group, wherein the aryl group defined as $P_1$ unsubstituted or substituted with any one selected from the group consisting of a C1 to C20 aliphatic chain linked to an aromatic ring, a C3 to C30 aliphatic ring linked to an aromatic ring, and combinations thereof.

[Chemical Formula 2]

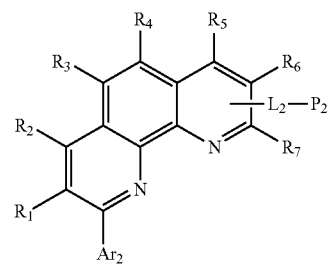

In the Chemical Formula 2, each of $R_1$ to $R_7$ independently represents any one selected from the group consisting of hydrogen, a C1 to C20 monovalent aliphatic chain group and a C3 to C30 monovalent aliphatic ring group, $L_2$ represents any one selected from the group consisting of a single bond, a substituted or unsubstituted C5 to C60 arylene group, a substituted or unsubstituted C4 to C60 heteroarylene group, and combinations thereof, $Ar_2$ represents a substituted or unsubstituted C5 to C60 aryl group or a substituted or unsubstituted C4 to C60 heteroaryl group, $P_2$ represents a substituted or unsubstituted C4 to C60 heteroaryl group, wherein the heteroaryl group defined as $P_2$ unsubstituted or substituted with any one selected from a group consisting of a C1 to C20 aliphatic chain linked to an aromatic heterocyclic ring, a C3 to C30 aliphatic ring linked to an aromatic heterocyclic ring, and combinations thereof.

The n-type charge generation layer includes, as a host, both of a compound represented by the Chemical Formula 1 and containing an aryl group of $P_1$ and a compound represented by the Chemical Formula 2 and containing a heteroaryl group of $P_2$. Thus, the n-type charge generation layer may lower driving voltage, and improve efficiency and lifespan of the organic electroluminescence device as well as improve the electrical stability of the device because the compounds can improve the electron injection and migration abilities of the n-type charge generation layer.

Each of the compound represented by the Chemical Formula 1 and the compound represented by the Chemical Formula 2 includes phenanthroline in which at least one hydrogen atom of at least one aromatic ring is substituted. The phenanthroline in which at least one hydrogen atom of at least one aromatic ring is substituted has a p electron-rich $sp^2$ hybrid, and contains electron-rich nitrogen atoms N. Thus, the phenanthroline in which at least one hydrogen atom of at least one aromatic ring is substituted has excellent electron transfer characteristics. Further, the phenanthroline contains two electron-rich nitrogen atoms N. The phenanthroline binds to the dopant of the n-type charge generation layer n-CGL, for example, an alkali metal or alkaline earth metal compound to form a gap state. The gap state allows a Fermi level of the organic compound to shift to a level adjacent to the lowest unoccupied molecular orbital (LUMO) level. This may reduce an energy level difference between the n-type charge generation layer n-CGL and the p-type charge generation layer p-CGL, such that electron injection to and migration in the n-type charge generation layer n-CGL are promoted. Further, this may improve electron injection and transfer characteristics from the n-type charge generation layer n-CGL to an adjacent electron transport layer ETL, thereby reducing a driving voltage of the device. In addition, a dopant (e.g., an alkali metal or alkaline earth metal compound) doped into the n-type charge generation layer n-CGL may interact with nitrogen atoms of phenanthroline to form ionic bonds. This may prevent the dopant made of an alkali metal or alkaline earth metal compound from diffusing into the electron transport layer or the p-type charge generation layer p-CGL adjacent thereto, thereby preventing efficiency and lifespan degradation of the organic electroluminescence device.

The compound represented by the Chemical Formula 1 is a phenanthroline compound having substituting aryl and is rich in p-electron and has a conjugated structure via $sp^2$ hybridization, thereby to have excellent intermolecular interaction due to p-p stacking, and thus to improve intermolecular electron transfer.

The compound represented by the Chemical Formula 2 is a phenanthroline compound containing a hetero atom. The compound represented by the Chemical Formula 2 has a larger electron affinity (EA) value than that of the compound represented by the Chemical Formula 1. Thus, the compound represented by the Chemical Formula 2 may have promoted interaction with the dopant material such as an alkali metal or an alkaline earth metal compound to smoothly form a gap state. Further, the layer containing the compound represented by the Chemical Formula 2 may have a lowered energy barrier with an adjacent layer. Thus, the n-type charge generation layer n-CGL containing the compound represented by the Chemical Formula 2 is excellent in the electron injection characteristics of receiving electrons from the p-type charge generation layer p-CGL and transferring the electrons into electron transport layer ETL.

In the organic electroluminescence device, the n-type charge generation layer n-CGL contains a mixture between the compound represented by the Chemical Formula 1 and the compound represented by the Chemical Formula 2. Thus, the organic electroluminescence device has both of an advantage of the compound represented by Chemical Formula 1, that is, excellent electron transfer characteristics for transferring electrons received from the p-type charge generation layer p-CGL to the electron transport layer ETL via strong intermolecular interaction, and an advantage of the compound represented by the Chemical Formula 2, that is, improved injection and transfer characteristics of electron generated from the p-type charge generation layer p-CGL into the electron transport layer ETL via ionic bonds resulting from excellent binding interaction with alkali metal (dopant). Thus, the n-type charge generation layer n-CGL accepting electrons may have enhanced stability against anion, thereby to lower the driving voltage of the device and improve the device performance and lifespan. Further, electrical stability and durability during long-time operation prevent diffusion of alkali metal. Effective electron injection and migration characteristics may be achieved by controlling charge mobility and injection amount, such that optimal charge balancing in each light-emission layer in each stack is achieved.

In this way, the organic electroluminescence device has a lowered driving voltage, and an improved efficiency and lifespan.

In one embodiment, in each of the Chemical Formula 1 and the Chemical Formula 2, each of $L_1$ and $L_2$ may represent a single bond, or represent continuous bonding, at a para-position, meta-position or ortho-position, between at least two groups selected from a group consisting of an arylene group and a heteroaryl group. Specifically, $L_1$ or $L_2$ may represent symmetrical bonding or asymmetrical bonding between at least two groups selected from a group consisting of an arylene group and a heteroaryl group.

In one embodiment of the present disclosure, in the Chemical Formula 2, $Ar_2$ includes a continuously bonded structure between at least two selected from a group consisting of an aryl ring and a heteroaryl ring. An aryl group defined as $Ar_2$ may or may not include any one selected from the group consisting of a C1 to C20 aliphatic chain connected to the continuously bonded structure, a C3 to C30 aliphatic ring connected to the continuously bonded structure, and combinations thereof.

In one embodiment of the present disclosure, in the Chemical Formula 2, $L_2$ includes a continuously bonded structure between at least two selected from a group consisting of an aryl ring and a heteroaryl ring. $L_2$ may or may not include any one selected from the group consisting of a C1 to C20 aliphatic chain connected to the continuously bonded structure, a C3 to C30 aliphatic ring connected to the continuously bonded structure, and combinations thereof.

Specifically, in the Chemical Formula 2, $Ar_2$ may include any one selected from the group consisting of a phenyl group, an alkylphenyl group, a biphenyl group, an alkylbiphenyl group, a halophenyl group, an alkoxyphenyl group, a haloalkoxyphenyl group, a cyanophenyl group, a silylphenyl group, a naphthyl group, an alkylnaphthyl group, a halonaphthyl group, a cyanonaphthyl group, a silylnaphthyl group, a phenylnaphthyl group, a pyridyl group, an alkylpyridyl group, a halopyridyl group, a cyanopyridyl group, an alkoxypyridyl group, a silylpyridyl group, a phenylpyridyl group, a pyrimidyl group, a halopyrimidyl group, a cyanopyridimyl group, a alkoxypyrimidyl group, a phenylpyrimidyl group, a quinolinyl group, an isoquinolinyl group, a phenylquinolinyl group, a quinoxalinyl group, a pyrazinyl group, a quinazolinyl group, a naphthyridinyl group, a benzothiophenyl group, a benzofuranyl group, a dibenzothiophenyl group, an arylthiazolyl group, a dibenzofuranyl group, a fluorenyl group, a carbazoyl group, an imidazolyl group, a carbolinyl group, a phenanthrenyl group, a terphenyl group, a terpyridinyl group, a phenylterpyridinyl group, a triphenylenyl group, a fluoranthenyl group, a diazafluorenyl group, and combinations thereof.

$Ar_2$ may further have or may not have an additional substituent. The additional substituent may include any one selected from the group consisting of a C1 to C20 alkyl group having or free of substituting halogen, a C1 to C20 alkoxy group having or free of substituting halogen, halogen, a cyano group, a carboxy group, a carbonyl group, an amine group, a C1 to C20 alkylamine group, a nitro group, a hydrazyl group, a sulfonic acid group, a C1 to C20 alkylsilyl group, a C1 to C20 alkoxysilyl group, a C3 to C30 cycloalkylsilyl group, a C5 to C30 arylsilyl group, a C5 to C30 aryl group, a C4 to C30 heteroaryl group, and combinations thereof.

Specifically, in the Chemical Formula 2, $L_2$ represents a single bond or includes a consecutively bonded structure of at least two selected from a group consisting of an aryl ring and a heteroaryl ring. Alternatively, $L_2$ may include any one selected from the group consisting of a phenylene group, an alkylphenylene group, a cyanophenylene group, a naphthylene group, an alkylnaphthylene group, a biphenylene group, an alkylbiphenylene group, an anthracenylene group, a triphenylene group, a pyrenylene group, a benzothiophenylene group, a benzofuranylene group, a dibenzothiophenylene group, an arylthiazolylene group, a dibenzofuranylene group, a fluorenylene group, a triphenylenylene and combinations thereof.

In one embodiment of the present disclosure, the n-type charge generation layer contains the compound represented by the Chemical Formula 1 and the compound represented by the Chemical Formula 2 in a weight ratio range of 5:95 to 95:5, specifically, 10:90 to 90:10.

When the n-type charge generation layer contains the compound represented by the Chemical Formula 1 and the compound represented by Chemical Formula 2 in the above defined content ratio range, the n-type charge generation layer may effectively improve the injection and migration characteristics of the electron.

The n-type charge generation layer contains both of the compound represented by the Chemical Formula 1 and the compound represented by the Chemical Formula 2 as a host material thereof, and further contains dopants, thereby to be configured as a host-dopant system.

The dopant may include any one selected from the group consisting of an alkali metal, an alkaline earth metal, an alkali metal compound, an alkaline earth metal compound, an organic complex of an alkali metal, an organic complex of an alkaline earth metal, and combinations thereof.

Specifically, the alkali metal may include any one selected from the group consisting of Li, Na, K, Rb, Cs, Fr, Yb and combinations thereof. Specifically, each of the alkaline earth metal and the alkaline earth metal compound may include any one selected from the group consisting of Be, Mg, Ca, Sr, Ba, Ra, and combinations thereof.

In the n-type charge generation layer, a doping concentration of the dopant may be in a range from 0.5% to 10% by volume based on a total volume of the organic compound. The n-type charge generation layer may further contain the dopant to enhance electron injection characteristics into the n-type charge generation layer.

In the device with a stack of light-emission sub-stacks, a total driving voltage of the device may be higher than a sum of the driving voltages of the light-emission sub-stacks. In addition, the device with a stack of light-emission sub-stacks may have a device efficiency degradation compared to a device having a single light emission layer. In this regard, when the n-type charge generation layer is doped with a dopant such as an alkali metal or an alkaline earth metal, the host material and the dopant in the n-type charge generation layer may form a charge transport complex via the binding interaction, thereby creating a new gap state. Thus, the energy level difference between the n-type charge generation layer and the p-type charge generation layer, and the energy level difference between the n-type charge generation layer and the electron transport layer are reduced to improve electron injection and migration.

However, when the device is driven for a long time, a charge transfer rate and injection amount changes due to the diffusion of the dopant such as an alkali metal into the layer adjacent to the n-type charge generation layer. Thus, the driving voltage of the device may increase and device efficiency and lifespan may be lowered. For this reason, in accordance with the present disclosure, the n-type charge generation layer contains both of the compound represented by the Chemical Formula 1 and the compound represented by the Chemical Formula 2 as a host material thereof. Thus, an effective binding interaction between the dopant and the host material can be induced, thereby to prevent the diffusion of the alkali metal due to electrical stability and durability of the n-type charge generation layer. Further, due to the effective electron injection and migration characteristics of the n-type charge generation layer, the electron injection amount may be controlled for optimizing the charge balance in the light-emission layer in each sub-stack, thereby to improve the efficiency and lifespan of the device.

The n-type charge generation layer may be a single layer structure, or a multi-layer structure including a stack of at least a first layer and a second layer. As described above, the n-type charge generation layer may contain a compound represented by the Chemical Formula 1 and a compound represented by Chemical Formula 2 in a single layer structure. Alternatively, the n-type charge generation layer is a multi-layer structure including a stack of a first layer and a second layer. In this case, the first layer may contain both of a compound represented by the Chemical Formula 1 and a compound represented by the Chemical Formula 2.

When the n-type charge generation layer has a multi-layer structure, a third layer may be included in addition to the second layer. In addition, when the n-type charge generation layer has a multi-layer structure, a layer (second or third layer) other than a layer (first layer) containing both of the compound represented by the Chemical Formula 1 and the compound represented by Chemical Formula 2 may contain only one of the compound represented by the Chemical Formula 1 and the compound represented by Chemical Formula 2.

Further, the layer (second or third layer) other than the layer (first layer) containing both of the compound represented by the Chemical Formula 1 and the compound represented by Chemical Formula 2 may further contain a dopant as described above together with the host of the n-type charge generation layer. Also, the n-type charge generation layer may be stacked such that the first layer is interposed between the p-type charge generation layer and the second layer, or such that the second layer is interposed between the p-type charge generation layer and the first layer.

In addition, the p-type charge generation layer may be of a layer type or a doping type. When the p-type charge generation layer is of the layer type, the p-type charge generation layer may contain an electron attracting material or a hole injection layer material. For example, the p-type charge generation layer may contain HAT-CN (hexaazatriphenylenehexacarbonitrile), TCNQ (tetracyanoquinodimethane), MoOx (molybdenum oxide), and the like. When the p-type charge generation layer is of the doping type, the p-type charge generation layer may contain a hole transport material (host) and the electron attracting material or hole injection layer material as a p-type dopant doped into the host.

Further, the hole transport material (host) can act to facilitate transport of the hole. The hole transport material may include any one selected from the group consisting of, for example, NPD (N,N-dinaphthyl-N,N'-diphenyl benzidine)(N,N'-bis(naphthalene-1-yl)-N,N'-bis(phenyl)-2,2'-dimethylbenzidine), TPD (N,N'-bis-(3-methylphenyl)-N,N'-bis-(phenyl)-benzidine), and MTDATA (4,4',4-Tris(N-3-methylphenyl-N-phenyl-amino)-triphenylamine). However, the present disclosure is not limited thereto. The p-type dopant may include a metal oxide, an organic material such as tetrafluoro-tetracyanoquinodimethane (F4-TCNQ), HAT-CN (hexaazatriphenylenehexacarbonitrile), hexaazatriphenylene, or etc., or a metal material such as $V_2O_5$, MoOx, $WO_3$, etc. The present disclosure is not limited thereto. The metal may include any one selected from the group consisting of Al, Cu, Fe, Pb, Zn, Au, Pt, W, In, Mo, Ni, Ti, and alloys of at least two thereof.

The charge generation layer CGL may be embodied as a PN junction charge generation layer in which the n-type charge generation layer n-CGL and the p-type charge generation layer p-CGL are adjacent to each other and are bonded to each other.

FIG. 1 is a schematic cross-sectional view of a tandem-type organic electroluminescence device with two light-emission sub-stacks according to an exemplary first embodiment of the present disclosure. As shown in FIG. 1, the organic electroluminescent device 100 according to the first embodiment of the present disclosure includes a first electrode 110, a second electrode 120, a first light-emission sub-stack 140 located between the first electrode 110 and the second electrode 120 and including a first light-emission layer, a second light-emission sub-stack 150 located between the first light-emission sub-stack 140 and the second electrode 120 and including a second light-emission layer, and a charge generation layer CGL 130 located between the first and second light-emission sub-stacks 140 and 150. As shown, the charge generation layer CGL 130 include a stack of an n-type charge generation layer 131 contacting the first light-emission sub-stack 140 and a p-type charge generation layer 132 contacting the second light-emission sub-stack 150.

The first electrode 110 acts as an anode and feeds a hole into the light-emission layer. In addition, the first electrode may contain a conductive material with a high work function to facilitate the feeding of the hole. The first electrode 110 may also be made of a conductive material, for example, indium-tin-oxide (ITO), indium-zinc-oxide (IZO) or zinc-oxide (ZnO). Further, the second electrode 120 acts as a cathode for injecting electrons and may be made of a conductive material having a small work function, for example, aluminum (Al), magnesium (Mg), or aluminum-magnesium alloy (AlMg).

Also, the first light-emission sub-stack 140 may include a light-emission layer and the second light-emission sub-stack 150 may include a light-emission layer. Each of the light-emission layers may emit red R, green G and blue B light beams, and may be made of a phosphorescent material or a fluorescent material.

When each of the light-emission layers emits red light, and when each of the light-emission layers is made of a phosphorescent material, each of the light-emission layers may contain: a host material including CBP (carbazole biphenyl) or mCP (1,3-bis (carbazol-9-yl); and dopants doped into the host and including at least any one selected from the group consisting of PIQIr(acac) (bis(1-phenylisoquinoline)acetylacetonate iridium), PQIr(acac) (bis(1-phenylquinoline)acetylacetonate iridium), PQIr (tris(1-phenylquinoline)iridium), PtOEP (octaethylporphyrin platinum), and combinations thereof. Alternatively, when each of the light-emission layers emits red light, and when each of the light-emission layers is made of a fluorescent material, each of the light-emission layers may contain PBD:Eu(DBM)3(Phen) or perylene. However, the present disclosure is not limited thereto.

Also, when each of the light-emission layers emits green light, and when each of the light-emission layers is made of a phosphorescent material, each of the light-emission layers may contain: a host material that includes CBP or mCP; and dopants doped into the host and including Ir(ppy)3 (fac tris(2-phenylpyridine)iridium). Alternatively, when each of the light-emission layers emits green light, and when each of the light-emission layers is made of a fluorescent material, each of the light-emission layers may contain Alq3 (tris(8-hydroxyquinolino)aluminum). However, the present disclosure is not limited thereto.

When each of the light-emission layers emits blue light, and when each of the light-emission layers is made of a phosphorescent material, each of the light-emission layers may contain: a host material that includes CBP or mCP; and dopants doped into the host and including (4,6-F2ppy) 2Irpic. Alternatively, when each of the light-emission layers emits blue light, and when each of the light-emission layers is made of a fluorescent material, each of the light-emission layers may contain at least any one selected from the group consisting of spiro-DPVBi, spiro-6P, distyrylbenzene (DSB), distyrylarylene (DSA), PFO-based polymer and PPV-based polymer and combinations thereof. However, the present disclosure is not limited thereto.

Each of the light-emission sub-stacks 140 and 150 may further include any one selected from the group consisting of a hole injection layer HIL, a hole transport layer HTL, an electron transport layer ETL, an electron injection layer EIL, and combinations thereof. Each of the light-emission sub-stacks 140 and 150 may further include a known functional layer may as appropriate as needed.

According to an embodiment of the present disclosure, the organic electroluminescence device 100 having a tandem structure includes the charge generation layer CGL 130 between the first light-emission sub-stack 140 and the second light-emission sub-stack 150 in order to increase a current efficiency of each of the light-emission layers EML, and to distribute charges smoothly. That is, the charge generation layer CGL 130 is located between the first light-emission sub-stack 140 and the second light-emission sub-stack 150. That is, the first light-emission sub-stack 140 and the second light-emission sub-stack 150 are connected via the charge generation layer 130.

According to an embodiment of the present disclosure, the organic electroluminescence device 100 may include a first charge generation layer and a second charge generation layer. In more detail, the first charge generation layer may be located between the first light-emission sub-stack 140 and the second light-emission sub-stack 150, while the second charge generation layer may be located between the second light-emission sub-stack 150 and an additional light-emission sub-stack. Also, the second light-emission sub-stack 150 and the additional light-emission sub-stack are connected via the second charge generation layer.

As used herein, the terms "first", "second" and the like are added for convenience to respectively refer to light emission layers respectively included in the plurality of light-emission sub-stacks. The terms "first", "second" and the like may be omitted to describe the common function between the light emission layers.

The hole injection layer HIL may facilitate the injection of holes. The hole injection layer may be made of at least one selected from a group of consisting of, for example, CuPc (cupper phthalocyanine), PEDOT (poly(3,4)-ethylenedioxythiophene), PANI (polyaniline), NPD (N,N-dinaphthyl-N,N'-diphenyl benzidine) and combinations thereof. However, the present disclosure is not limited thereto.

The hole transport layer HTL may contain, as a hole transport material, a material electrochemically stabilized via cationization (i.e., by losing electrons). Alternatively, the hole transport layer may contain a material that produces a stable radical cation as a hole transport material. Alternatively, the hole transport material may contain aromatic amine to be easily cationized. In one example, the hole transport material may include at least one selected from a group of consisting of NPD (N,N-dinaphthyl-N,N'-diphenylbenzidine; N,N'-bis(naphthalene-1-yl)-N,N'-bis(phenyl)-2,2'-dimethylbenzidine), TPD (N,N'-bis-(3-methylphenyl)-N,N'-bis-(phenyl)-benzidine), spiro-TAD (2,2',7,7'-tetrakis (N,N-dimethylamino)-9,9-spirofluorene), MTDATA (4,4',4-Tris(N-3-methylphenyl-N-phenylamino)-triphenylamine), and combinations thereof. However, the present disclosure is not limited thereto.

In addition, the electron transport layer ETL receive electrons from the second electrode 120 and can transfer the supplied electrons to the light-emission layers EML. The electron transport layer EML also serves to facilitate the transport of electrons. In more detail, the electron transport layer EML contains an electron transport material electrochemically stabilized by being anionic (i.e., by obtaining electrons). Alternatively, the electron transport material may produce the stable radical anion. The electron transport material may alternatively contain a heterocyclic ring to be easily anionized by heteroatoms. In one example, the electron transport material may include at least one selected from a group of consisting of, for example, Alq3 (tris(8-hydroxyquinolino)aluminum), Liq (8-hydroxyquinolinolatolithium), PBD (2-(4-biphenylyl)-5-(4-tert-butylphenyl)-1, 3,4oxadiazole), TAZ (3-(4-biphenyl)4-phenyl-5-tert-butylphenyl-1,2,4-triazole), spiro-PBD, BAlq (bis(2-methyl-8-quinolinolate)-4-(phenylphenolato)aluminium), SAlq, TPBi (2,2',2-(1,3,5-benzinetriyl)-tris(1-phenyl-1-H-benzimidazole), oxadiazole, triazole, phenanthroline, benzoxazole and benzthiazole. However, the present disclosure is not limited thereto.

The electron injection layer EIL serves to facilitate the injection of electrons and contains an electron injection material. The electron injection material may include, but is not limited to, at least one selected from a group of consisting of Alq3 (tris(8-hydroxyquinolino)aluminum), PBD, TAZ, spiro-PBD, BAlq, SAlq and combinations thereof. Alternatively, the electron injection layer EIL may be made of a metal compound. The metal compound may include, but is not limited to, at least one selected from a group of consisting of, for example, LiQ, LiF, NaF, KF, RbF, CsF, $FrF$, $BeF_2$, $MgF_2$, $CaF_2$, $SrF_2$, $BaF_2$ and $RaF_2$.

Figure 2:
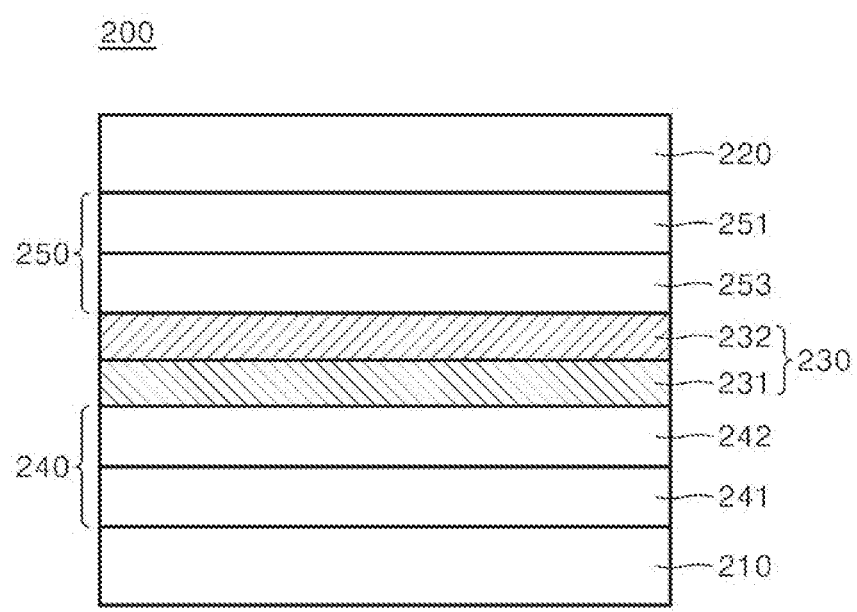
FIG. 2 is a cross-sectional view schematically illustrating an organic electroluminescence device according to an embodiment of the present disclosure.

Next, FIG. 2 is a schematic cross-sectional view of a tandem type organic electroluminescence device with two light-emission sub-stacks according to an second embodiment of the present disclosure. In FIG. 2, the organic electroluminescence device 200 sequentially includes, in a direction from an anode 210 toward a cathode 220, a first light-emission sub-stack 240 and a second light-emission sub-stack 250. As shown, the first light-emission sub-stack 240 includes a first light-emission layer 241, and the second light-emission sub-stack 250 includes a second light-emission layer 251. The first light-emission sub-stack 240 further includes an electron transport layer 242, and the second light-emission sub-stack 250 further includes a hole transport layer 253. In addition, the electron transport layer 242, a charge generation layer 230, and the hole transport layer 253 can be sequentially stacked in this order between the first light-emission layer 241 and the second light-emission layer 251.

Further, the charge generation layer CGL 230 generates charges or separates charges into holes and electrons to supply electrons and holes to the first and second light-emission sub-stacks 140 and 150. For example, a n-type charge generation layer n-CGL 231 supplies electrons to the electron transport layer 242 of the first light-emission sub-stack 240. The electron transport layer 242 supplies electrons to the first light-emission layer 241 adjacent to the first electrode 210. In one example, a p-type charge generation layer p-CGL 232 supplies holes to the second hole transport layer 253 of the second light-emission sub-stack 250. The second hole transport layer 253 supplies holes to the second light-emission layer 252.

As described above, the n-type charge generation layer n-CGL 231 includes a compound represented by the Chemical Formula 1 as a host material. In addition, doping dopants such as an alkali metal or alkaline earth metal compound into the host material of the n-type charge generation layer n-CGL 231 can enhance the electron injection characteristics of the n-type charge generation layer n-CGL 231.

Figure 3:
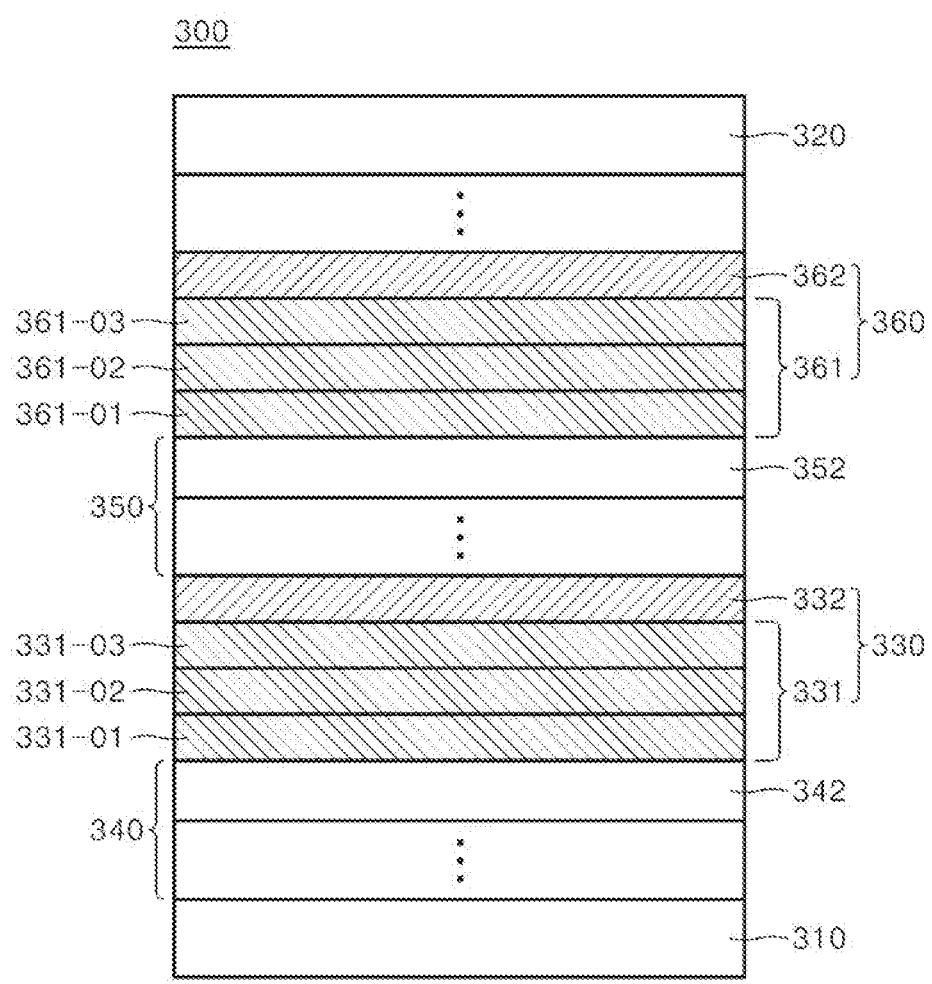
FIG. 3 is a cross-sectional view schematically illustrating an organic electroluminescence device according to an embodiment of the present disclosure.

FIG. 3 is a schematic cross-sectional view of an organic electroluminescence device according to an exemplary third embodiment of the present disclosure. In FIG. 3, the organic electroluminescence device 300 includes a first n-type charge generation layer n-CGL 331 having a stacked multilayer structure in which a first layer 331-02 containing both of a compound represented by the Chemical Formula 1 and a compound represented by the Chemical Formula 2 is vertically sandwiched between a second layer 331-01 and a third layer 331-03. Each of the second layer 331-01 and the third layer 331-03 may contain only one of the compound represented by the Chemical Formula 1 and the compound represented by the Chemical Formula 2.

Similarly, the organic electroluminescence device 300 includes a second n-type charge generation layer n-CGL 361 having a stacked multilayer structure in which a first layer 361-02 containing both of a compound represented by the Chemical Formula 1 and a compound represented by the Chemical Formula 2 is vertically sandwiched between a second layer 361-01 and a third layer 361-03. Each of the second layer 361-01 and the third layer 361-03 may contain only one of the compound represented by the Chemical Formula 1 and the compound represented by the Chemical Formula 2.

Further, the organic electroluminescence device 300 includes sequentially a first light-emission sub-stack 340 and a second light-emission sub-stack 350 in this order in a direction from an anode 310 to a cathode 320. The first light-emission sub-stack 340 includes a stack of a first light-emission layer and a first electron transport layer 342. The second light-emission sub-stack 350 includes a stack of a second light-emission layer and a second electron transport layer 352. In addition, a first charge generation layer 330 including a stack of the first n-type charge generation layer 331 and a first p-type charge generation layer 332 is interposed between the first light-emission sub-stack 340 and the second light-emission sub-stack 350. A second charge generation layer 360 including a stack of the second n-type charge generation layer 361 and a second p-type charge generation layer 362 is also interposed between the second light-emission sub-stack 350 and the cathode 320.

In FIG. 3, a symbol ':' represents a multilayer structure including a stack of organic layers such as a hole transport layer and a light-emission layer, etc. For example, a third light-emission sub-stack, a third charge generation layer, and a fourth light-emission sub-stack can be disposed between the second charge generation layer 360 and the cathode 320. Hereinafter, in FIGS. 4 and 5, the symbol ':' represents a multilayer structure including a stack of organic layers such as a hole transport layer and a light-emission layer, etc.

Figure 4:
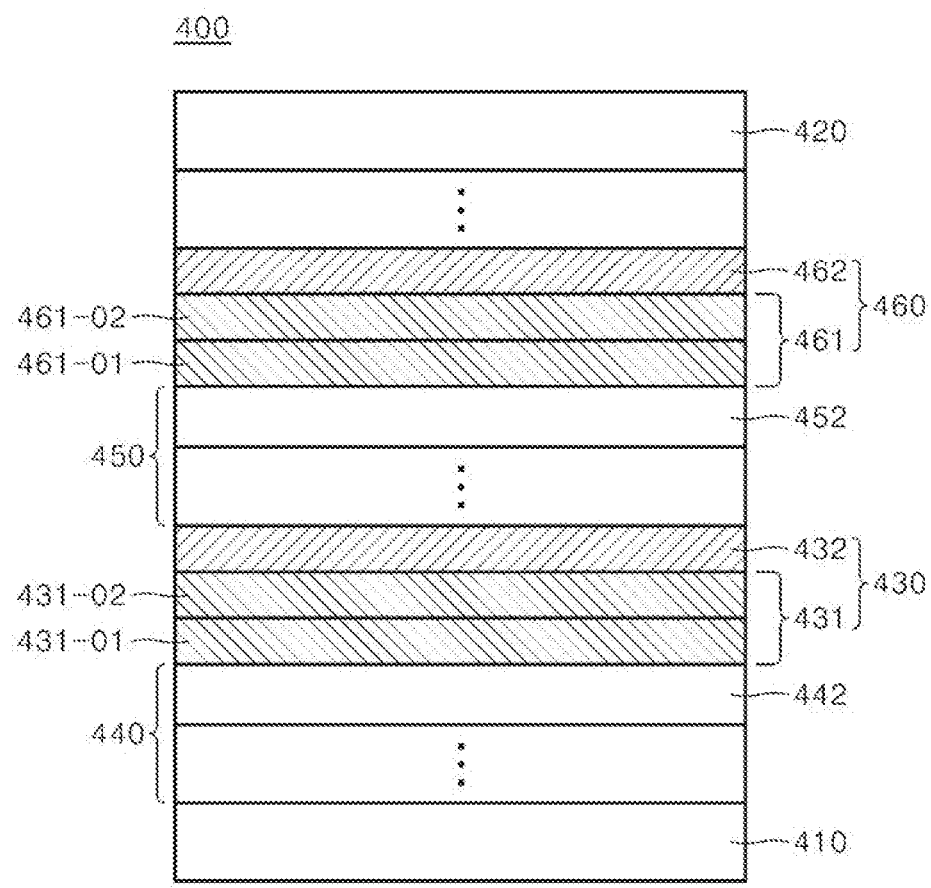
FIG. 4 is a cross-sectional view schematically illustrating an organic electroluminescence device according to an embodiment of the present disclosure.

Next, FIG. 4 is a schematic cross-sectional view of an organic electroluminescence device according to an exemplary fourth embodiment of the present disclosure. In FIG. 4, in an organic electroluminescence device 400, a first n-type charge generation layer n-CGL 431 includes a stack of a first layer 431-02 containing both of a compound layer represented by the Chemical Formula 1 and a compound represented by Chemical Formula 2, and a second layer 431-01. The second layer 431-01 may contain only one of the compound represented by the Chemical Formula 1 and the compound represented by the Chemical Formula 2. Likewise, a second n-type charge generation layer n-CGL 461 includes a stack of a first layer 461-02 containing both of a compound represented by the Chemical Formula 1 and a compound represented by Chemical Formula 2, and a second layer 461-01. The second layer 461-01 may contain only one of the compound represented by the Chemical Formula 1 and the compound represented by the Chemical Formula 2.

Further, the organic electroluminescence device 400 includes a first light-emission sub-stack 440 and a second light-emission sub-stack 450 sequentially in a direction from an anode 410 to a cathode 420. The first light-emission sub-stack 440 includes a stack of a first light-emission layer and a first electron transport layer 442. Also, the second light-emission sub-stack 450 includes a stack of a second light-emission layer and a second electron transport layer 452. Further, a first charge generation layer 430 including a stack of the first n-type charge generation layer 431 and a first p-type charge generation layer 432 is interposed between the first light-emission sub-stack 440 and the second light-emission sub-stack 450. A second charge generation layer 460 including a stack of the second n-type charge generation layer 461 and a second p-type charge generation layer 462 is interposed between the second light-emission sub-stack 450 and the cathode 420.

Figure 5:
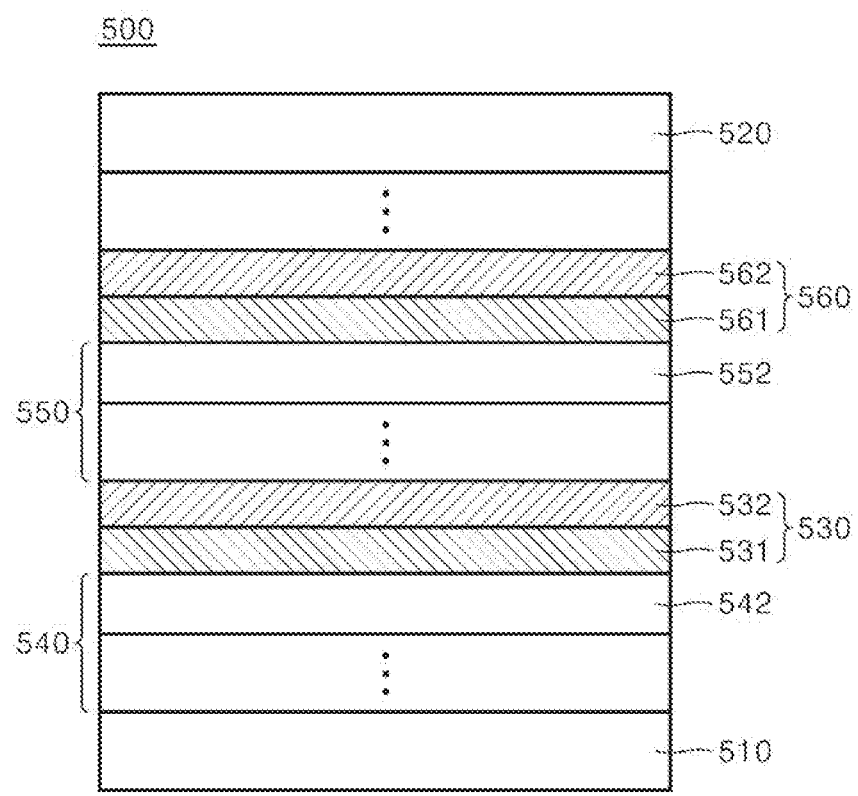
FIG. 5 is a cross-sectional view schematically illustrating an organic electroluminescence device according to an embodiment of the present disclosure.

FIG. 5 is a schematic cross-sectional view of an organic electroluminescence device according to an exemplary fifth embodiment of the present disclosure. In FIG. 5, in an organic electroluminescence device 500, each of a first n-type charge generation layer n-CGL 531 and a second n-type charge generation layer n-CGL 561 includes a single layer containing both of a compound represented by the Chemical Formula 1 and a compound represented by the Chemical Formula 2.

Further, the organic electroluminescence device 500 sequentially includes a first light-emission sub-stack 540 and a second light-emission sub-stack 550 in this order in a direction from an anode 510 to a cathode 520. The first light-emission sub-stack 540 includes a stack of a first light-emission layer and a first electron transport layer 542. The second light-emission sub-stack 550 includes a stack of a second light-emission layer and a second electron transport layer 552. Further, a first charge generation layer 530 including a stack of the first n-type charge generation layer 531 and a first p-type charge generation layer 532 is interposed between the first light-emission sub-stack 540 and second light-emission sub-stack 550. A second charge generation layer 560 including a stack of the second n-type charge generation layer 561 and a second p-type charge generation layer 562 is interposed between the second light-emission sub-stack 550 and the cathode 520.

Figure 6:
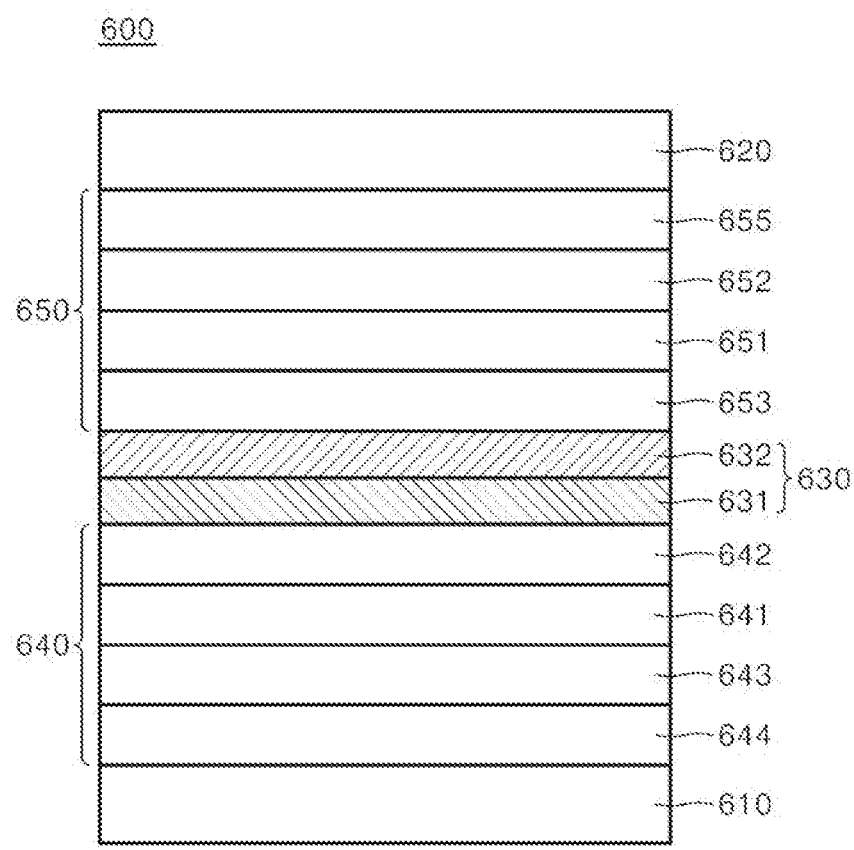
FIG. 6 is a cross-sectional view schematically illustrating an organic electroluminescence device according to an embodiment of the present disclosure.

FIG. 6 is a schematic cross-sectional view of an organic electroluminescence device according to an exemplary sixth embodiment of the present disclosure. In FIG. 6, an organic electroluminescence device 600 sequentially includes a first light-emission sub-stack 640, an n-type charge generation layer 631 of a charge generation layer 630, a p-type charge generation layer 632 of the charge generation layer 630, and a second light-emission sub-stack 650 in this order in a direction from an anode 610 toward a cathode 620. The first light-emission sub-stack 640 sequentially includes a first hole injection layer 644, a first hole transport layer 643, a first light-emission layer 641 and a first electron transport layer 642 in a direction from the anode 610 to the n-type charge generation layer 631. The second light-emission sub-stack 650 sequentially includes a second hole transport layer 653, a second light-emission layer 651, a second electron transport layer 652, and a second electron injection 655 in a direction from the p-type charge generation layer 632 to the cathode 620.

In one implementation of the present disclosure, an energy gap between the lowest unoccupied molecular orbital (LUMO) level of the compound represented by the Chemical Formula 1 and the lowest unoccupied molecular orbital (LUMO) level of the compound represented by the Chemical Formula 2 may satisfy following Relationship 1 and Relationship 2:

[Chemical Formula 1]$_{LUMO}$–[p-type dopant]$_{LUMO}$≥
[Chemical Formula 1]$_{LUMO}$–[Chemical Formula 2]$_{LUMO}$       [Relationship 1]

[Chemical Formula 1]$_{LUMO}$–[p-type charge generation layer]$_{LUMO}$≥[Chemical Formula 1]$_{LUMO}$–
[Chemical Formula 2]$_{LUMO}$       [Relationship 2]

In each of the Relationship 1 and Relationship 2, [Chemical Formula 1]$_{LUMO}$ refers to the lowest unoccupied molecular orbital (LUMO) level of the compound represented by the Chemical Formula 1. [Chemical Formula 2]$_{LUMO}$ refers to the lowest unoccupied molecular orbital (LUMO) level of the compound represented by the Chemical Formula 2. [p-type dopant]$_{LUMO}$ refers to the lowest unoccupied molecular orbital (LUMO) level of the p-type dopant. [p-type charge generation layer]$_{LUMO}$ refers to the lowest unoccupied molecular orbital (LUMO) level of the p-type charge generation layer.

Figure 7:
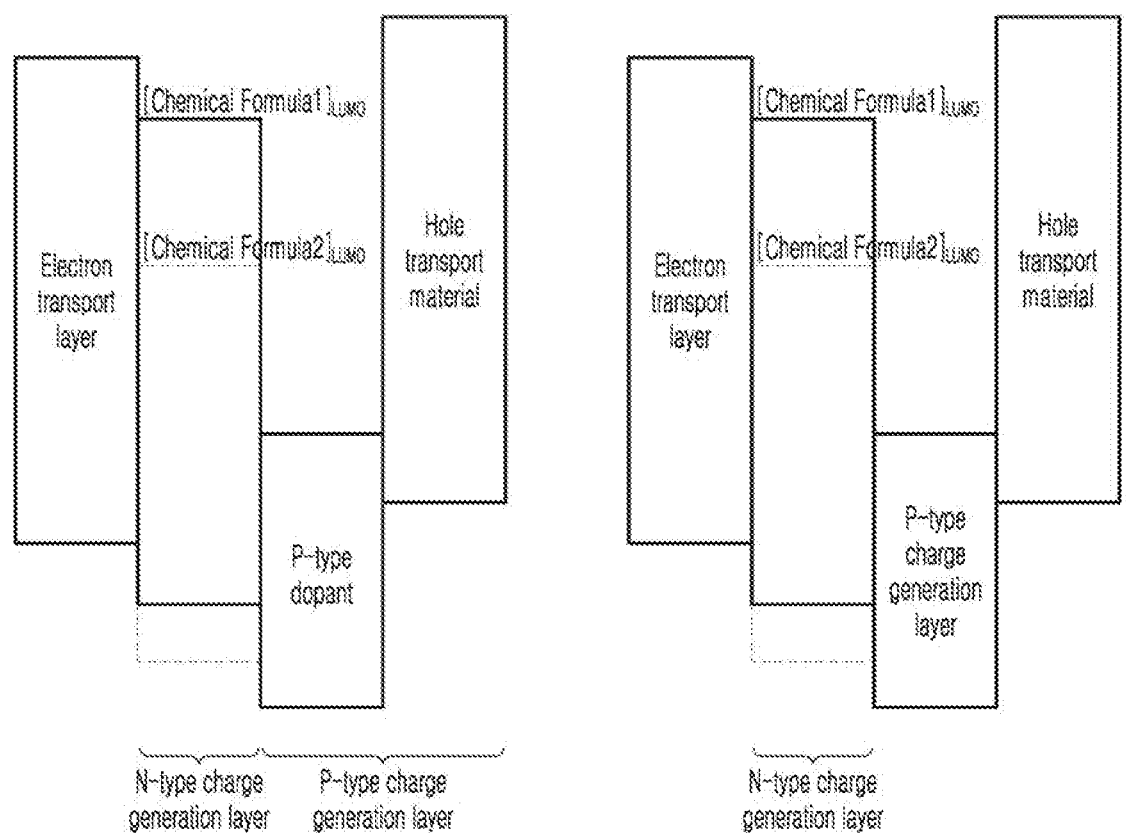
FIG. 7 is an energy diagram illustrating energy levels of a compound represented by a Chemical Formula 1 and a compound represented by a Chemical Formula 2 included in an n-type charge generation layer, an electron transport layer ETL, a hole transport layer HTL, and a p-type charge generation layer or a hole transport material and p-type dopant of the p-type charge generation layer in an organic electroluminescence device according to an exemplary embodiment of the present disclosure.

Next, FIG. 7 is an energy diagram illustrating energy levels of a compound represented by a Chemical Formula 1 and a compound represented by a Chemical Formula 2 included in an n-type charge generation layer, an electron transport layer ETL, a hole transport layer HTL, and a p-type charge generation layer or a hole transport material and p-type dopant of the p-type charge generation layer in an organic electroluminescence device according to an exemplary embodiment of the present disclosure.

In addition, the compound represented by the Chemical Formula 1 is selected so that the lowest unoccupied molecular orbital (LUMO) level of the compound represented by the Chemical Formula 1 is equal to or lower than the lowest unoccupied molecular orbital (LUMO) level of the electron transport layer ETL. Further, the compound represented by the Chemical Formula 2 is selected so that the lowest unoccupied molecular orbital (LUMO) level of the compound represented by the Chemical Formula 2 is equal to or higher than the lowest unoccupied molecular orbital (LUMO) level of the p-type dopant.

When the n-type charge generation layer n-CGL contains a mixture of a compound represented by the Chemical Formula 2 and a compound represented by the Chemical Formula 1, or includes a stack of a layer of a compound represented by the Chemical Formula 1 and a layer of a compound represented by the Chemical Formula 2, the lowest unoccupied molecular orbital (LUMO) level of the compound represented by Chemical Formula 2 is present between the lowest unoccupied molecular orbital (LUMO) levels of the p-type charge generation layer p-CGL and the compound represented by Chemical Formula 1. Thus, the lowest unoccupied molecular orbital (LUMO) level of the compound represented by Chemical Formula 2 is equal to or lower than the lowest unoccupied molecular orbital (LUMO) level of the compound represented by Chemical Formula 1 and is equal to or higher than the lowest unoccupied molecular orbital (LUMO) level of the p-type charge generation layer p-CGL, thereby to reduce an energy level difference between the n-type charge generation layer n-CGL and the p-type charge generation layer p-CGL. This may allow the electron injection and migration to the n-type charge generation layer n-CGL to be promoted. Further, this may improve electron injection and transport characteristics from the n-type charge generation layer n-CGL to the adjacent electron transport layer ETL. Thus, this may reduce the driving voltage of the organic electroluminescence device and contribute to the efficiency and lifespan increase of the device.

The organic electroluminescence device according to the present disclosure may be applied to an organic light emitting display device and an organic electroluminescence display device. In one example, FIG. 20 is a schematic cross-sectional view of an organic light emitting display device to which an organic electroluminescence device according to an exemplary embodiment of the present disclosure is applied.

Figure 20:
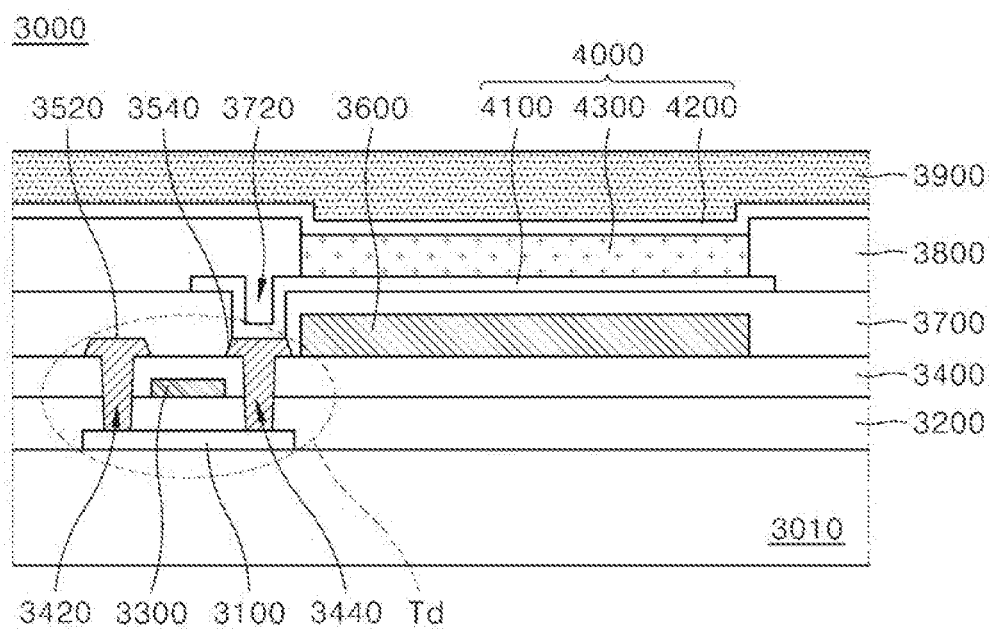
FIG. 20 is a cross-sectional view schematically illustrating an organic light emitting display device including an organic electroluminescence device according to an exemplary embodiment of the present disclosure.

As shown in FIG. 20, an organic light emitting display device 3000 may include a substrate 3010, an organic electroluminescence device 4000, and an encapsulation film 3900 covering the organic electroluminescence device 4000. On the substrate 3010, a driving thin-film transistor TFT, which is a driving device, and the organic electroluminescence device 4000, which is connected to the driving thin-film transistor TFT, are positioned.

In addition, on the substrate 3010, a gate line and a data line, which define a pixel region, a power line extending parallel to and spaced from either the gate line or the data line, a switching thin-film transistor connected to the gate line and data line, a storage capacitor connected to the power line and one electrode of the switching thin-film transistor are formed.

Further, the driving thin-film transistor Td is connected to the switching thin-film transistor, and includes a semiconductor layer 3100, a gate electrode 3300, a source electrode 3520 and a drain electrode 3540. As shown, the semiconductor layer 3100 is formed on the substrate 3010, and is made of an oxide semiconductor material or polycrystalline silicon. When the semiconductor layer 3100 is made of an oxide semiconductor material, a light-blocking pattern may be formed below the semiconductor layer 3100. The light-blocking pattern prevents light from being incident on the semiconductor layer 3100, thereby preventing the semiconductor layer 3010 from being deteriorated by light. Alternatively, when the semiconductor layer 3100 may be made of polycrystalline silicon, impurities may be doped into both edges of the semiconductor layer 3100.

On the semiconductor layer 3100, a gate insulating film 3200 made of an insulating material is formed over the entire face of the substrate 3010. The gate insulating film 3200 may be made of an inorganic insulating material such as silicon oxide or silicon nitride.

In addition, a gate electrode 3300 made of a conductive material such as metal is formed on the gate insulating film 3290 and in a region corresponding to a middle region of the semiconductor layer 3100. The gate electrode 3300 is connected to the switching thin-film transistor. Further, an interlayer insulating film 3400 made of an insulating material is formed on the gate electrode 3300 and over the entire face of the substrate 3010. The interlayer insulating film 3400 may be made of an inorganic insulating material such as silicon oxide or silicon nitride, or may be made of an organic insulating material such as benzocyclobutene or photo-acryl.

In addition, the inter-layer insulating film 3400 has first and second contact holes 3420 and 3440 defined therein for respectively exposing both lateral portions of the semiconductor layer 3100. The first and second contact holes 3420 and 3440 are spaced apart from the gate electrode 330 and disposed on both sides of the gate electrode 3300 respectively.

On the inter-layer insulating film 3400, the source electrode 3520 and drain electrode 3540 made of a conductive material such as a metal are disposed. The source electrode 3520 and drain electrode 3540 are disposed around the gate electrode 3300 and are spaced from each other. The source electrode 3520 and drain electrode 3540 contacts both sides of the semiconductor layer 3100 via the first and second contact holes 3420 and 3440, respectively. The source electrode 3520 is connected to a power line.

The semiconductor layer 3100, the gate electrode 3300, the source electrode 3520, and the drain electrode 3540 define the driving thin-film transistor Td. Further, the driving thin-film transistor Td has a coplanar structure in which the gate electrode 3300, the source electrode 3520, and the drain electrode 3540 are disposed in a coplanar manner on the semiconductor layer 3100.

Alternatively, the driving thin-film transistor Td may have an inverted staggered structure in which the gate electrode is located below the semiconductor layer, and the source electrode and the drain electrode are located above the semiconductor layer. In this case, the semiconductor layer may be made of amorphous silicon. In one example, the switching thin-film transistor may have substantially the same structure as the driving thin-film transistor Td.

In one example, the organic light emission display device 3000 may include a color filter 3600 that absorbs light generated from the organic electroluminescent device 4000. For example, the color filter 3600 may absorb red (R), green (G), blue (B), and white (W) light. In this instance, color filter patterns that absorb the red, green and blue light can be disposed separately on a pixel basis. Each of these color filter patterns can overlap with a corresponding organic light-emitting layer 4300 of the organic electroluminescent device 4000 that emits light having a corresponding wavelength. Adopting the color filter 3600 allows the organic light emission display device 3000 to render a full color range.

For example, when the organic light emission display device 3000 is of a bottom light emission type, the color filter 3600, which absorbs light, can be located above the inter-layer insulating film 3400 in a region of the organic electroluminescent device 4000. In an alternative embodiment, when the organic light emission display device 3000 is of a top light emission type, the color filter can be located on top of the organic electroluminescent device 4000, i.e., on top of the second electrode 4200. In one example, the color filter 3600 may have a thickness of 2 to 5 μm. In this connection, the organic electroluminescent device 4000 may be embodied as a white-light organic electroluminescent device having a tandem structure as shown in FIGS. 1 to 6.

In one example, a protective layer 3700 having a drain contact hole 3720 exposing the drain electrode 3540 of the driving thin-film transistor Td may be formed to cover the driving thin-film transistor Td. On the protective layer 3700, the first electrode 4100 connected to the drain electrode 3540 of the driving thin-film transistor Td via the drain contact hole 3720 may be formed on a pixel region basis.

The first electrode 4100 may act as an anode and may be made of a conductive material having a relatively higher work function value. For example, the first electrode 4100 may be made of a transparent conductive material such as ITO, IZO or ZnO. In one example, when the organic light emitting display device 3000 is of a top light emission type, a reflective electrode or a reflective layer may be further formed below the first electrode 4100. For example, the reflective electrode or reflective layer may be made of any one of aluminum (Al), silver (Ag), nickel (Ni), and aluminum-palladium-copper (APC alloy).

On the protective layer 3700, a bank layer 3800 covering an edge of the first electrode 4100 is formed. The bank layer 3800 exposes a center region of the first electrode 4100 corresponding to the pixel region. An organic light-emitting layer 4300 is formed on the first electrode 4100. In one example, the organic light-emitting layer 4300 may have at least two light emission sub-stacks shown in FIGS. 1 and 2. Accordingly, the organic electroluminescent device 4000 can have a tandem structure.

A second electrode 4200 is formed on the organic light-emitting layer 4300 and can be disposed over an entire display region and may be made of a conductive material having a relatively lower work function value and may act as a cathode. For example, the second electrode 4200 may be made of any one of aluminum (Al), magnesium (Mg), and aluminum-magnesium alloy (AlMg). In addition, the first electrode 4100, the organic light-emitting layer 4300 and the second electrode 4200 together define the organic electroluminescent device 4000.

On the second electrode 4200, the encapsulation film 3900 is formed to prevent external moisture from penetrating into the organic electroluminescent device 4000. Although not shown, the encapsulation film 3900 may have a triple layer structure in which a first inorganic layer and an organic layer and a second inorganic layer are sequentially stacked. However, the present invention is not limited thereto.

Hereinafter, an Example and a Comparative example of the present disclosure will be described. Such Example is only one embodiment of the present disclosure, and the present disclosure is not limited to the Example.

EXAMPLES

Hereinafter, compounds used in Example and Comparative Example were synthesized as follows.

Synthesis Example 1: PA-1 Synthesis

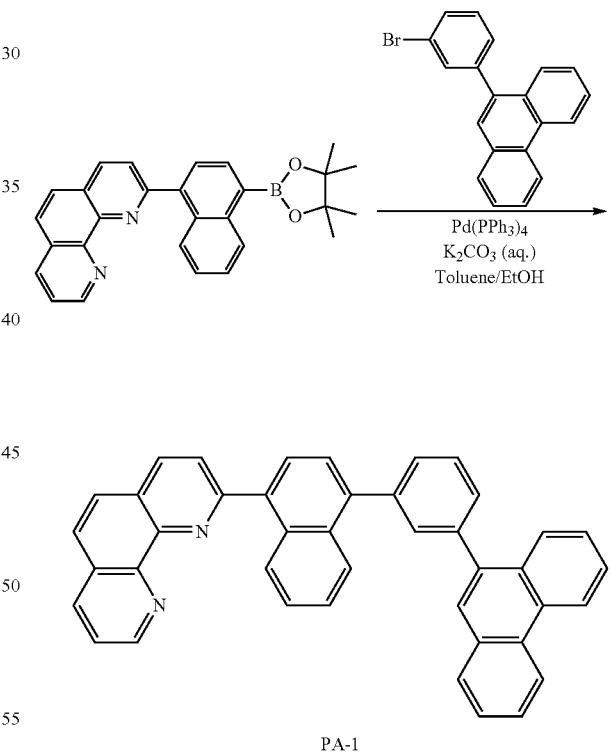

PA-1

2-(1-(4,4,5,5-tetramethyl-1,3,2-dioxaborolan-2-yl)naphthalen-4-yl)-1,10-phenanthroline (8.0 g, 18.50 mmol), 9-(3-bromophenyl)phenanthrene (7.0 g, 21.08 mmol), tetrakistriphenylphosphine palladium (0) (Pd(PPh₃)₄) (1.07 g, 0.93 mmol), 4M potassium carbonate aqueous solution (12 ml), toluene 35 ml, and ethanol 12 ml were input and mixed in a flask under a nitrogen atmosphere to form a mixture. The mixture was stirred while refluxed for 12 hours. After the reaction was completed, 50 ml of H₂O was added to a reaction product which in turn was stirred for 3 hours and then was filtered under reduced pressure, and was separated by a column chromatography using methylene chloride (MC) and hexane as an eluent. The separated product was recrystallized using MC to obtain the compound PA-1 (8.39 g, yield 81.2%).

Synthesis Example 2: PA-2 Synthesis

[Reaction Formula 2]

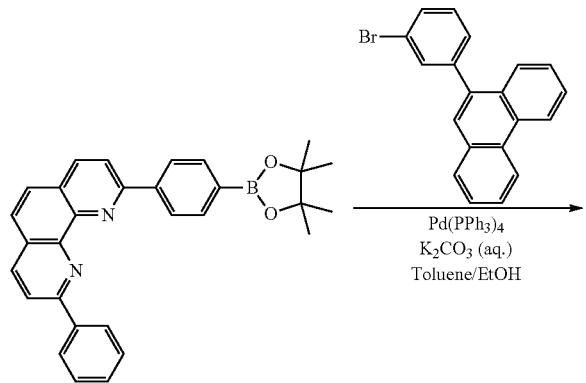

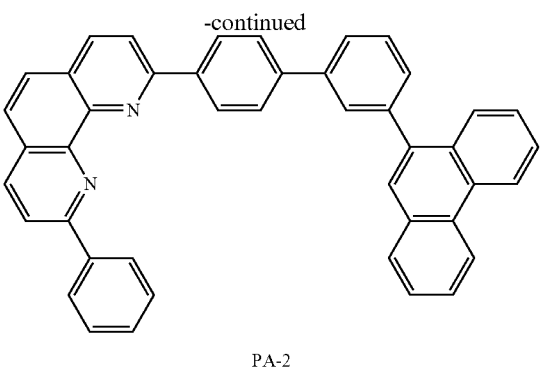

PA-2

2-(4-(4,4,5,5-tetramethyl-1,3,2-dioxaborolan-2-yl)phenyl)-9-phenyl-1,10-phenanthroline (7.0 g, 15.27 mmol), 9-(3-bromophenyl)phenanthrene (6.6 g, 19.85 mmol), tetrakistriphenylphosphine palladium (0) (Pd(PPh₃)₄) (0.93 g, 0.81 mmol), 4M potassium carbonate aqueous solution (12 ml), tolulene 35 ml, and ethanol 12 ml were input and mixed in a flask under a nitrogen atmosphere to form a mixture. The mixture was stirred while refluxed for 12 hours. After the reaction was completed, 50 ml of H₂O was added to a reaction product which in turn was stirred for 3 hours and then was filtered under reduced pressure, and was separated by a column chromatography using methylene chloride (MC) and hexane as an eluent. The separated product was recrystallized using MC to obtain the compound PA-2 (7.10 g, yield 79.6%).

Synthesis Example 3: PH-1 Synthesis

[Reaction Formula 3]

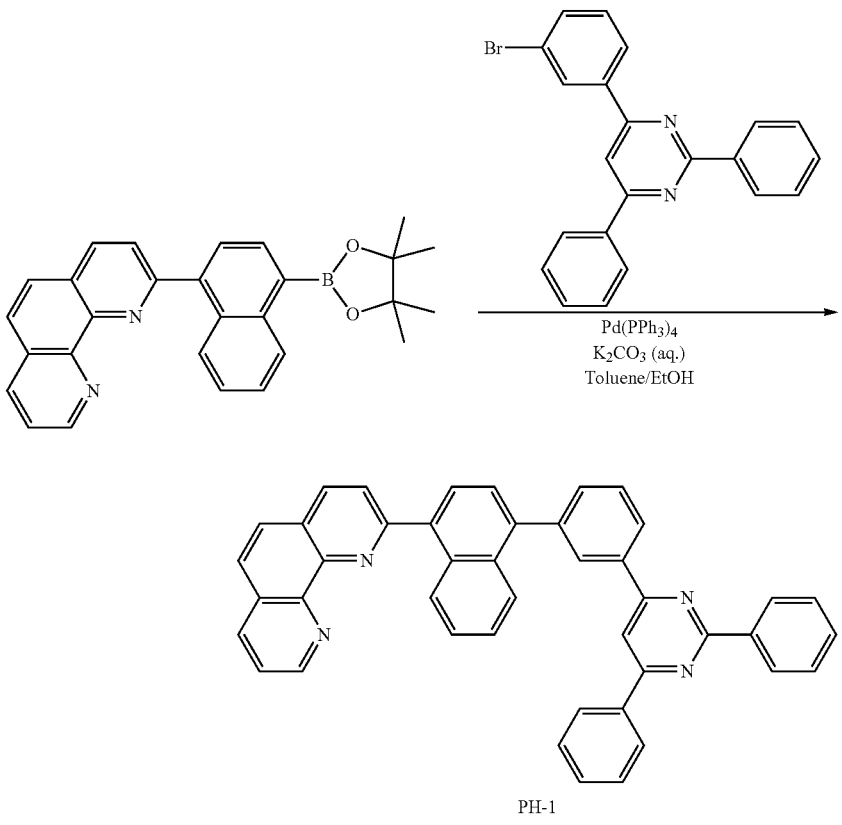

PH-1

2-(1-(4,4,5,5-tetramethyl-1,3,2-dioxaborolan-2-yl)naphthalen-4-yl)-1,10-phenanthroline (7.0 g, 16.19 mmol), 4-(3-bromophenyl)-2,6-diphenylpyrimidine (8.13 g, 21.05 mmol), tetrakistriphenylphosphine palladium (0) (Pd(PPh$_3$)$_4$) (0.93 g, 0.81 mmol), 4M potassium carbonate aqueous solution (12 ml), tolulene 35 ml, and ethanol 12 ml were input and mixed in a flask under a nitrogen atmosphere to form a mixture. The mixture was stirred while refluxed for 12 hours. After the reaction was completed, 50 ml of H$_2$O was added to a reaction product which in turn was stirred for 3 hours and then was filtered under reduced pressure, and was separated by a column chromatography using methylene chloride (MC) and hexane as an eluent. The separated product was recrystallized using MC to obtain the compound PH-1 (7.45 g, yield 75.2%).

Synthesis Example 4: PH-2 Synthesis

[Reaction Formula 4]

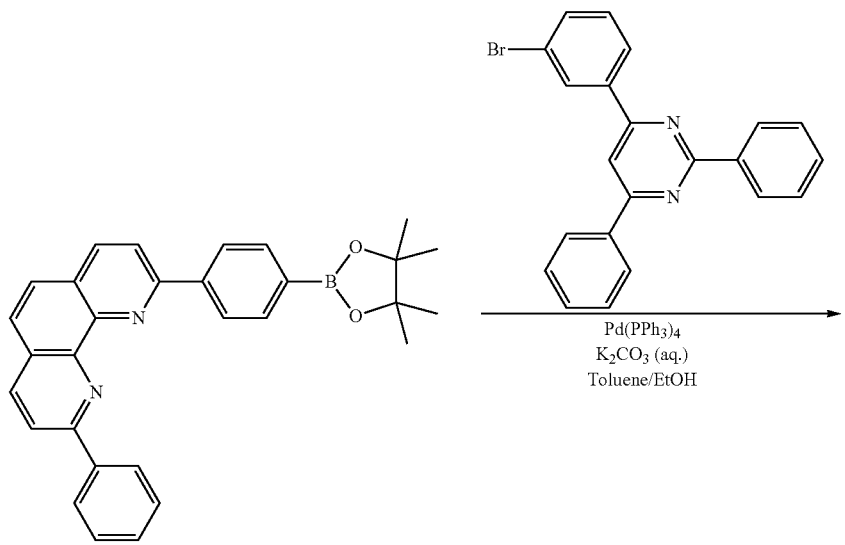

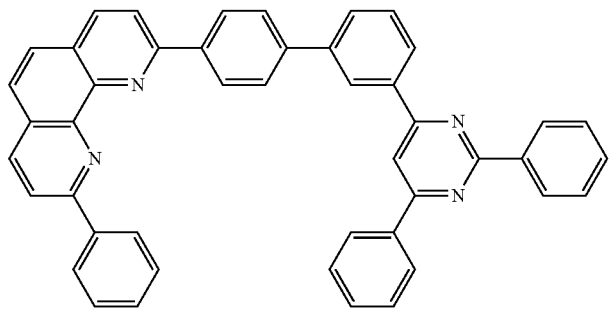

PH-2

2-(4-(4,4,5,5-tetramethyl-1,3,2-dioxaborolan-2-yl)phenyl)-9-phenyl-1,10-phenanthroline (7.0 g, 15.27 mmol), 4-(3-bromophenyl)-2,6-diphenylpyrimidine (7.7 g, 19.85 mmol), tetrakistriphenylphosphine palladium (0) (Pd (PPh$_3$)$_4$) (0.88 g, 0.76 mmol), 4M potassium carbonate aqueous solution (12 ml), tolulene 35 ml, and ethanol 12 ml were input and mixed in a flask under a nitrogen atmosphere to form a mixture. The mixture was stirred while refluxed for 12 hours. After the reaction was completed, 50 ml of H$_2$O was added to a reaction product which in turn was stirred for 3 hours and then was filtered under reduced pressure, and was separated by a column chromatography using methylene chloride (MC) and hexane as an eluent. The separated product was recrystallized using MC to obtain the compound PH-2 (7.09 g, yield 72.7%).

Example 1

In a vacuum chamber with a pressure of 5 to 7×10$^{-8}$ torr, following layers were sequentially deposited on an ITO substrate. A material of each layer is shown in Table 1.

<Organic Electroluminescent Device Structure>
ITO/HIL/HTL1/1$^{st}$ EML/ETL1/n-CGL/p-CGL/HTL2/2$^{nd}$ EML/ETL2/n-CGL/p-CGL/HTL3/3$^{rd}$ EML/ETL3/EIL/Al

TABLE 1

| Layer, abbreviation | Material, thickness |
|---|---|
| Cathode | Al, 2000 Å |
| Electron injection layer, EIL | LiF, 10 Å |
| Third electron transport layer, ETL3 | TmPyPB*, 100 Å |
| Third light-emission layer, EML3 | Blue light emission material layer, pyrylene based dopant 4 wt % doped into anthracene based host, 200 Å |
| Third hole transport layer, HTL3 | NPD, 200 Å |
| P-type charge transport layer, p-CGL | F4-TCNQ dopant 15 wt % doped into NPD host, 150 Å |
| N-type charge transport layer, n-CGL | Li dopant 2 wt % doped into PA-1 and PH-1 host, 150 Å, weight ratio of PA-1:PH-1 = (50:50) |
| Second electron transport layer, ETL2 | Alq3 |
| Second light-emission layer, EML2 | Yellow (YG) light emission material layer, Ir complex dopant 10 wt % doped into CBP host, 200 Å |
| Second hole transport layer, HTL2 | NPD, 200 Å |
| P-type charge transport layer, p-CGL | F4-TCNQ dopant 15 wt % doped into NPD host, 150 Å |
| N-type charge transport layer, n-CGL | Li dopant 2 wt % doped into PA-1 and PH-1 host, 150 Å, weight ratio of PA-1:PH-1 = 50:50 |
| First electron transport layer, ETL1 | TmPyPB, 100 Å |
| First light-emission layer, EML1 | Blue light emission material layer, pyrylene based dopant 4 wt % doped into anthracene-based host, 200 Å |
| First hole transport layer, HTL1 | NPD, 1000 Å |
| Hole transport layer, HIL | F4-TCNQ dopant 15 wt % doped into NPD host, 100 Å |
| Anode | ITO |

TmPyPB*: 1,3,5-Tri[(3-pyridyl)-phen-3-yl]benzene

Examples 2 to 4 and Comparative Examples 1 to 7

The host material PA-1 and PH-1=50:50 (weight ratio) of the n-type charge transport layer n-CGL in Example 1 was changed to materials as shown in Table 2 below. In this way, organic electroluminescent devices in accordance with Examples 2 to 4 and Comparative Examples 1 to 7 were fabricated.

TABLE 2

| Examples | Host material of n-type charge transport layer n-CGL |
|---|---|
| Example 2 | PA-2 and PH-1 (50:50) (weight ratio) |
| Example 3 | PA-2 and PH-2 (50:50) (weight ratio) |
| Example 4 | PA-1 and PH-2 (50:50) (weight ratio) |
| Comparative Example 1 | BPhen (Bathophenanthroline) |
| Comparative Example 2 | PA-1 |
| Comparative Example 3 | PA-2 |
| Comparative Example 4 | PA-1 and PA-2 (50:50) (weight ratio) |
| Comparative Example 5 | PH-1 |
| Comparative Example 6 | PH-2 |
| Comparative Example 7 | PH-1 and PH-2 (50:50) (weight ratio) |

Examples 5 to 10

The host material PA-2 and PH-2=50:50 (weight ratio) of the n-type charge transport layer n-CGL in Example 3 was changed to materials while a content ratio thereof varies, as shown in Table 3 below. In this way, organic electroluminescent devices in accordance with Examples 5 to 10 were fabricated.

TABLE 3

| Examples | Host material of n-type charge transport layer n-CGL |
|---|---|
| Comparative Example 3 | PA-2 |
| Example 5 | PA-2 and PH-2 (95:5) (weight ratio) |
| Example 6 | PA-2 and PH-2 (90:10) (weight ratio) |
| Example 7 | PA-2 and PH-2 (70:30) (weight ratio) |

TABLE 3-continued

| Examples | Host material of n-type charge transport layer n-CGL |
|---|---|
| Example 3 | PA-2 and PH-2 (50:50) (weight ratio) |
| Example 5 | PA-2 and PH-2 (30:70) (weight ratio) |
| Example 6 | PA-2 and PH-2 (10:90) (weight ratio) |
| Example 7 | PA-2 and PH-2 (5:95) (weight ratio) |
| Comparative Example 6 | PH-2 |

Experimental Example 1

Figure 8:
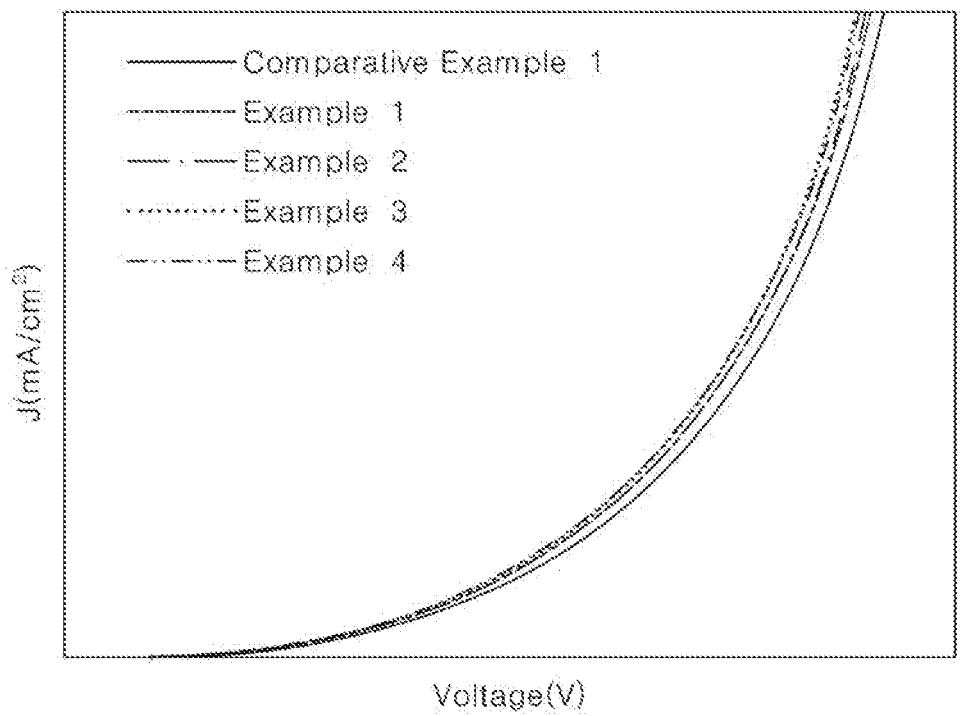
FIG. 8 is a graph illustrating a voltage-current density of devices of Examples 1-4 and Comparative Example 1.
Figure 9:
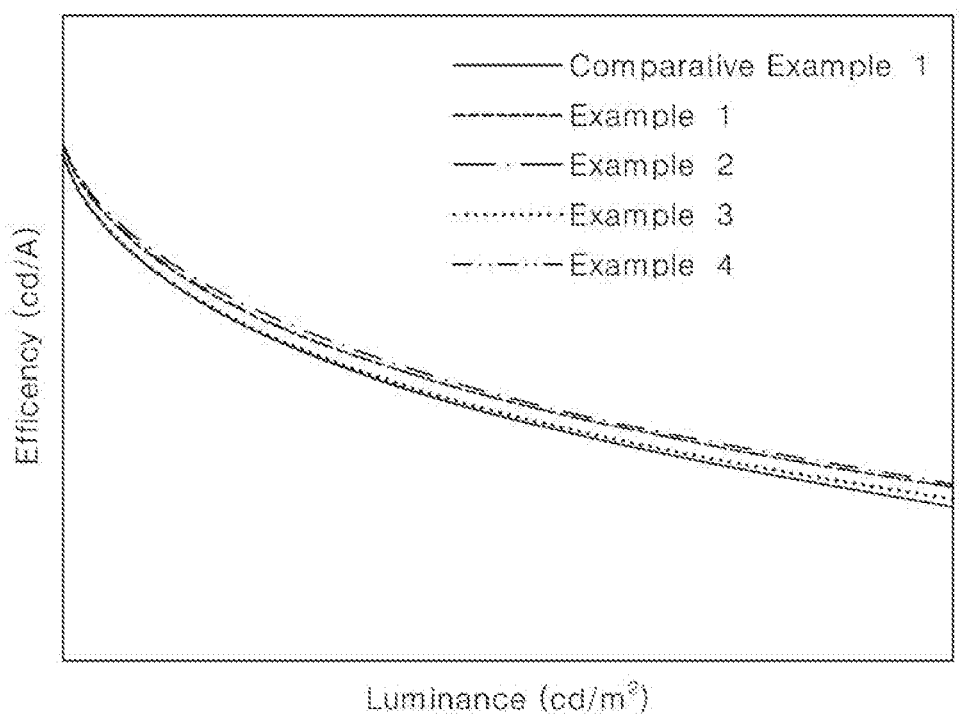
FIG. 9 is a graph illustrating a luminance-current efficiency of devices of Examples 1-4 and Comparative Example 1.
Figure 10:
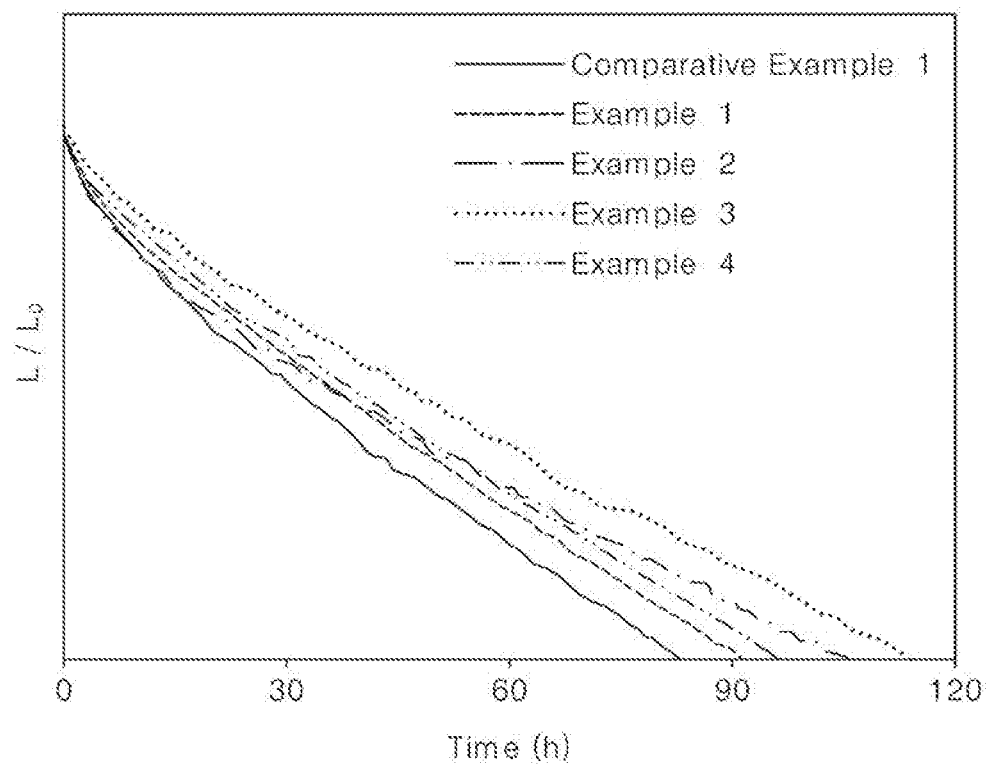
FIG. 10 is a graph illustrating lifespan characteristics of devices of Examples 1-4 and Comparative Example 1.
Figure 11:
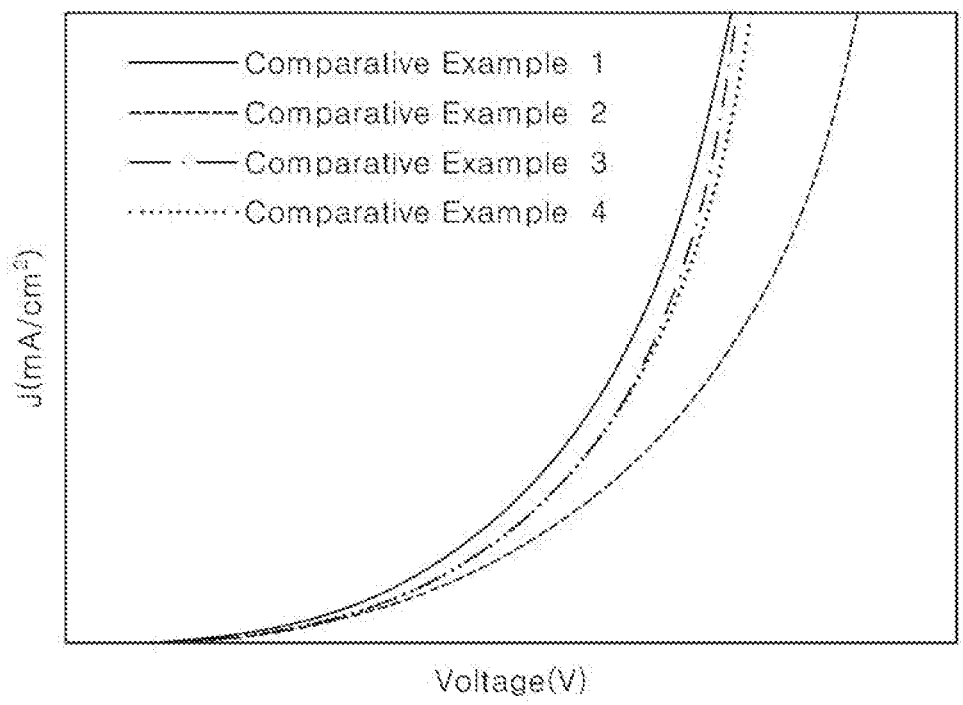
FIG. 11 is a graph illustrating a voltage-current density of devices of Comparative Examples 1-4.
Figure 12:
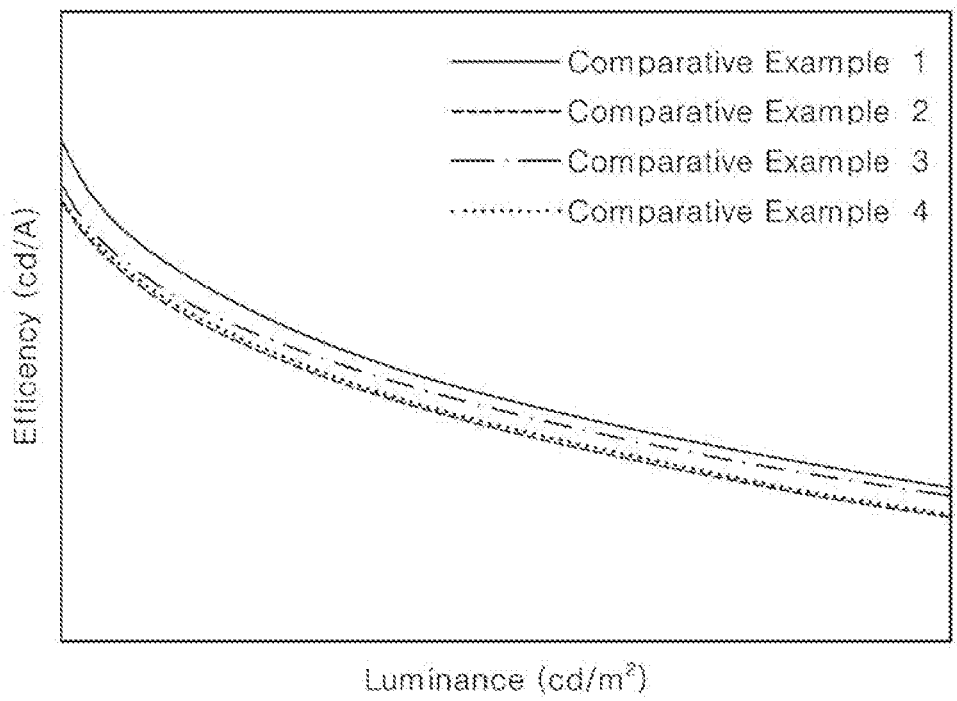
FIG. 12 is a graph illustrating a luminance-current efficiency of devices of Comparative Examples 1-4.
Figure 13:
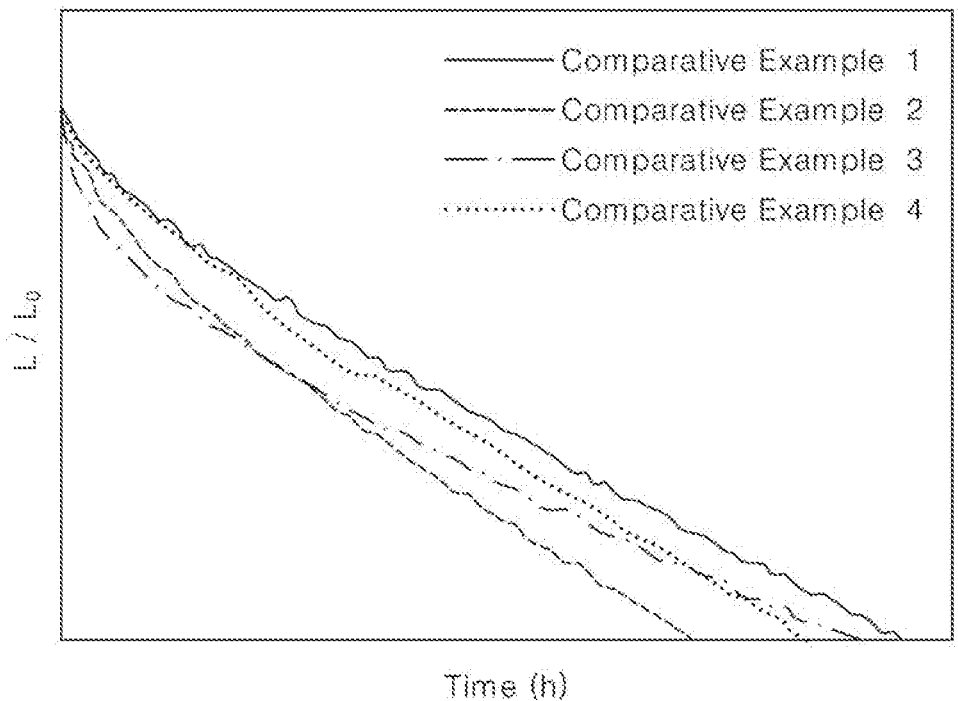
FIG. 13 is a graph illustrating lifespan characteristics of devices of Comparative Examples 1-4.
Figure 14:
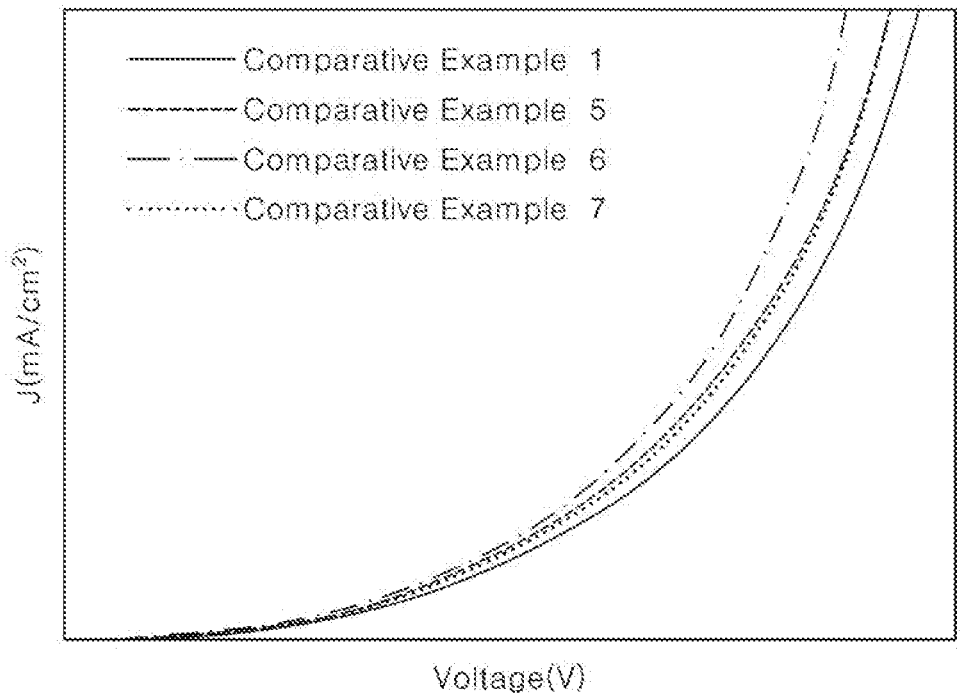
FIG. 14 is a graph illustrating a voltage-current density of devices of Comparative Examples 1, 5, 6 and 7.
Figure 15:
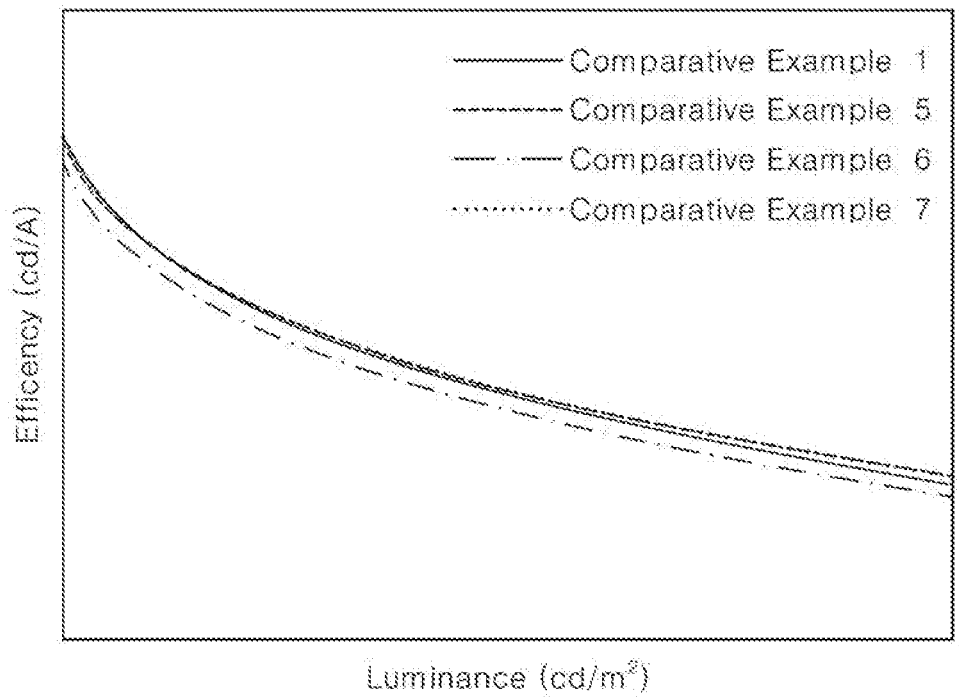
FIG. 15 is a graph illustrating a luminance-current efficiency of devices of Comparative Examples 1, 5, 6 and 7.
Figure 16:
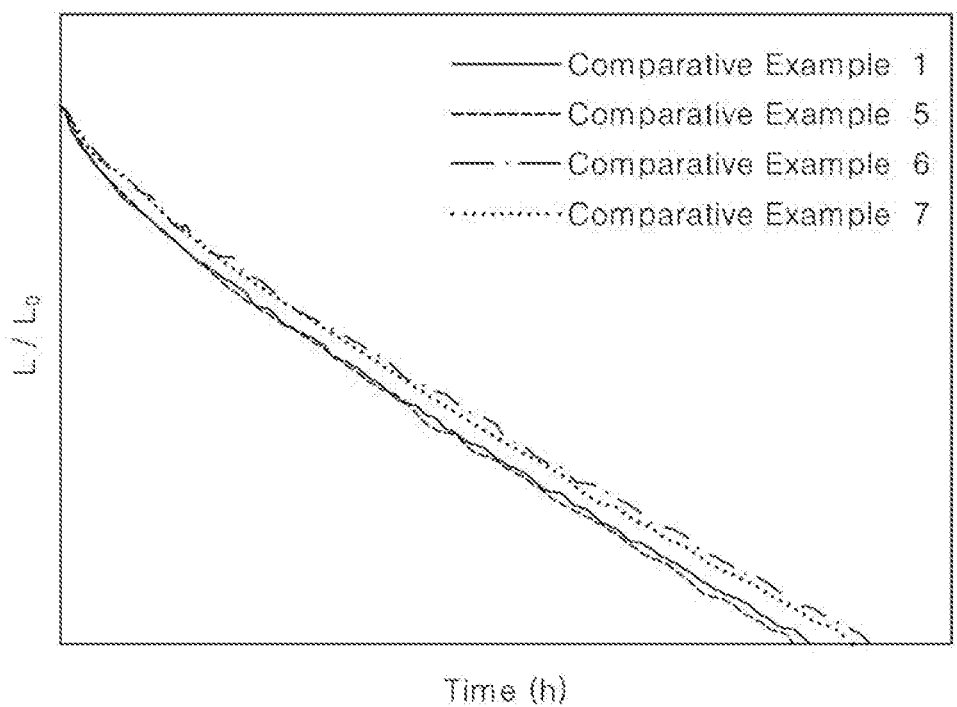
FIG. 16 is a graph illustrating lifespan characteristics of devices of Comparative Examples 1, 5, 6 and 7.
Figure 17:
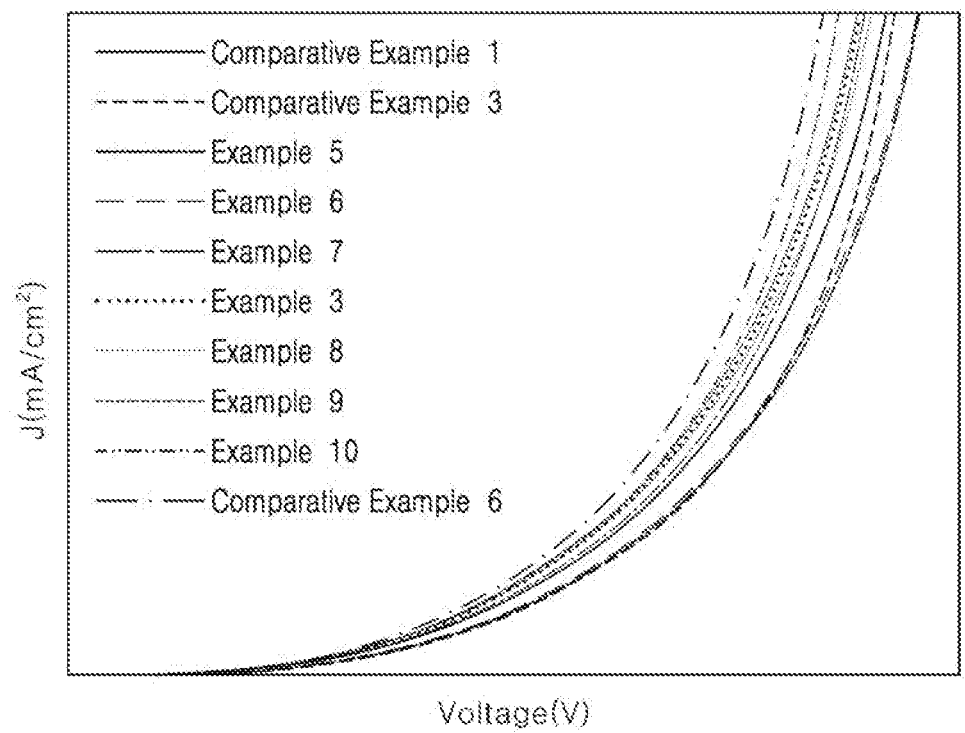
FIG. 17 is a graph illustrating a voltage-current density of devices of Examples 3, 5, 6, 7, 8, 9 and 10 and Comparative Examples 1, 3, 6.
Figure 18:
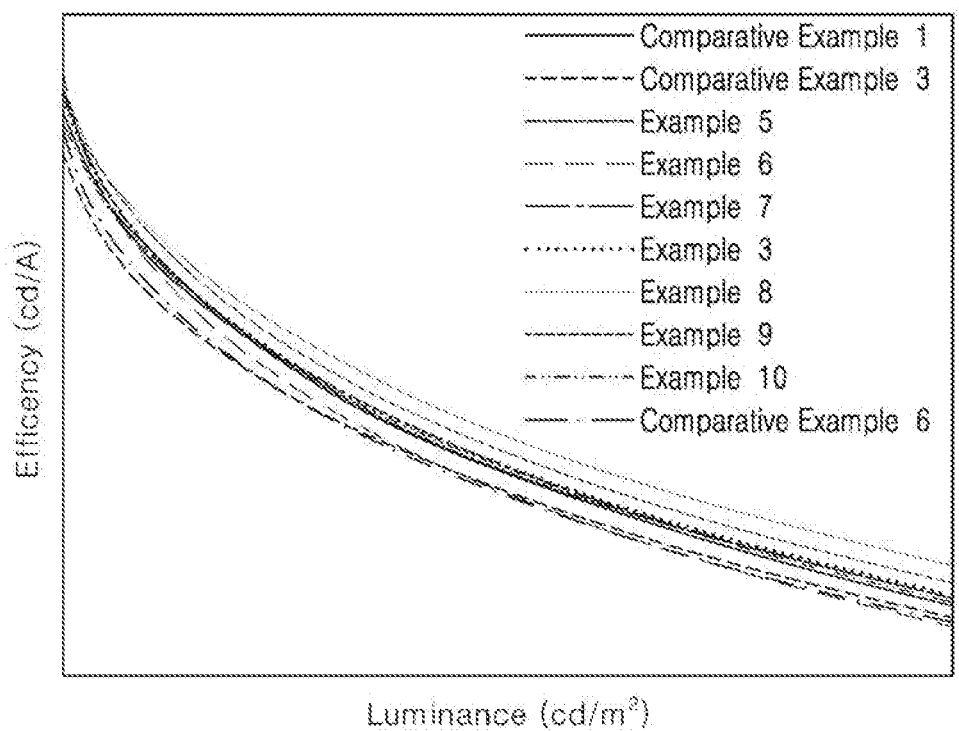
FIG. 18 is a graph illustrating a luminance-current efficiency of devices of Examples 3, 5, 6, 7, 8, 9 and 10 and Comparative Examples 1, 3, 6.
Figure 19:
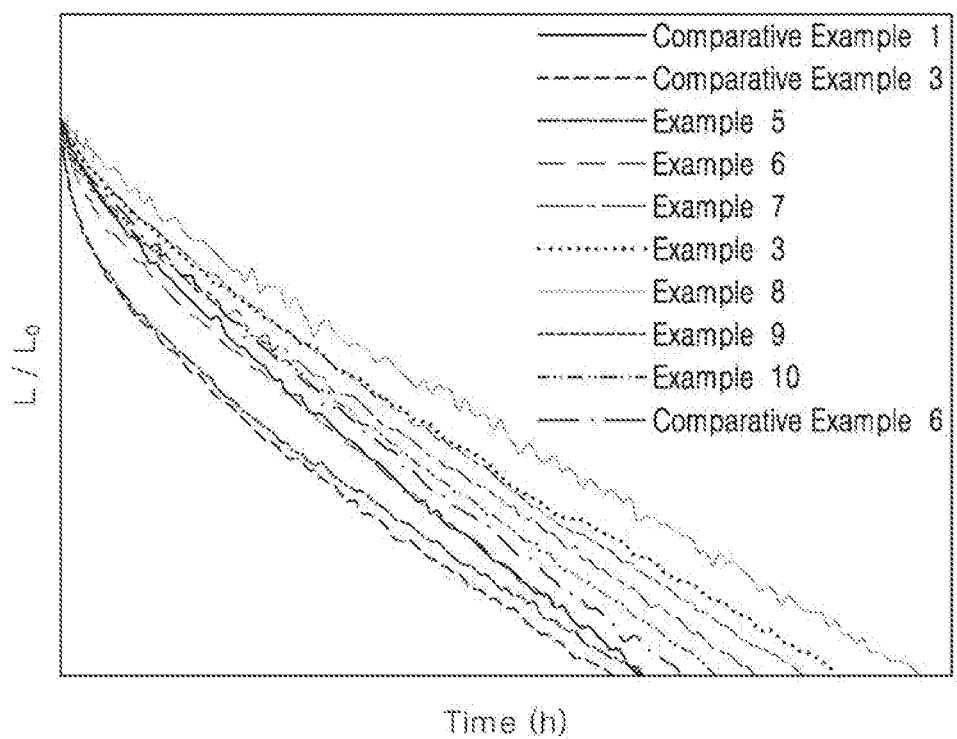
FIG. 19 is a graph illustrating lifespan characteristics of devices of Examples 3, 5, 6, 7, 8, 9 and 10 and Comparative Examples 1, 3, 6.

The driving characteristics of each of the organic electroluminescence devices fabricated in the Examples 1 to 7 and Comparative Examples 1 to 7 were evaluated. In addition, FIGS. 8 to 10 show the voltage-current density, luminance-current efficiency, and lifespan characteristics of each of Examples 1 to 4, as compared to Comparative Example 1, FIGS. 11 to 13 show the voltage-current density, luminance-current efficiency, and lifespan characteristics of each of Comparative Examples 2 to 4 compared with Comparative Example 1, FIGS. 14 to 6 show the voltage-current density, luminance-current efficiency, and lifespan characteristics of each of Comparative Examples 5 to 7 in comparison with Comparative Example 1, and FIGS. 17 to 19 show the voltage-current density, luminance-current efficiency, and lifespan characteristics of each of Examples 5 to 10 over varying content ratios as compared with Comparative Example 3 and Comparative Example 6 and show the voltage-current density, luminance-current efficiency, and lifespan characteristics of each of Examples 5 to 10 compared to Comparative Example 1.

Further, Table 4 and Table 5 show comparison results.

TABLE 4

| Examples | Voltage (V) | Luminance-external quantum efficiency (EQE) | Voltage-current density (Cd/A) | Lifespan (hr) |
|---|---|---|---|---|
| Example 1 | −0.09 | 101% | 102% | 101% |
| Example 2 | −0.09 | 102% | 103% | 126% |
| Example 3 | −0.14 | 100% | 101% | 137% |
| Example 4 | −0.13 | 102% | 101% | 114% |
| Comparative Example 2 | +0.43 | 97% | 96% | 75% |
| Comparative Example 3 | +0.25 | 100% | 97% | 95% |
| Comparative Example 4 | +0.21 | 97% | 96% | 89% |
| Comparative Example 5 | −0.17 | 100% | 101% | 99% |
| Comparative Example 6 | −0.24 | 98% | 100% | 108% |
| Comparative Example 7 | −0.13 | 100% | 102% | 106% |

As shown in Table 4, the devices of Examples 1 to 4 increased the lifespan and reduced the driving voltage compared to the devices of Comparative Examples 1 to 4 while maintaining the efficiency to be equal to or higher than those of the devices of Comparative Examples 1 to 4 at the current density of 10 mA/cm$^2$.

TABLE 5

| Examples | Voltage (V) | Luminance-external quantum efficiency (EQE) | Voltage-current density (Cd/A) | Lifespan (hr) |
|---|---|---|---|---|
| Comparative Example 3 | +0.25 | 100% | 97% | 95% |
| Example 5 | +0.19 | 100% | 100% | 101% |
| Example 6 | +0.17 | 100% | 99% | 102% |
| Example 7 | −0.03 | 101% | 100% | 120% |
| Example 3 | −0.14 | 101% | 101% | 137% |
| Example 8 | −0.14 | 103% | 102% | 150% |
| Example 9 | −0.12 | 102% | 101% | 130% |
| Example 10 | −0.13 | 100% | 100% | 114% |
| Comparative Example 6 | −0.24 | 98% | 100% | 108% |

As shown in Table 5, the devices of Examples 3, 5 to 10 increased the lifespan and reduced the driving voltage compared to the devices of Comparative Examples 3 and 6 while maintaining the efficiency to be equal to or higher than those of the devices of Comparative Examples 3 and 6 at the current density of 10 mA/cm$^2$.

As described above, the present disclosure is described with reference to the drawings. However, the present disclosure is not limited by the embodiments and drawings disclosed in the present specification. It will be apparent that various modifications may be made thereto by those skilled in the art within the scope of the present disclosure. Furthermore, although the effect resulting from the features of the present disclosure has not been explicitly described in the description of the embodiments of the present disclosure, it is obvious that a predictable effect resulting from the features of the present disclosure should be recognized.

What is claimed is:

1. An organic electroluminescence device comprising:
an anode and a cathode spaced from each other;
at least two light-emission sub-stacks located between the anode and the cathode, wherein each of the at least two light-emission sub-stacks includes at least one light-emission layer; and
a charge generation layer located between the two light-emission sub-stacks,
wherein the charge generation layer includes a stack of a n-type charge generation layer and a p-type charge generation layer,
wherein the n-type charge generation layer faces the anode,
wherein the p-type charge generation layer faces the cathode,
wherein the n-type charge generation layer contains a compound represented by Chemical Formula 1 and a compound represented by Chemical Formula 2:

[Chemical Formula 1]

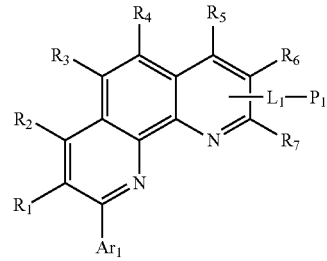

wherein, in the Chemical Formula 1, each of $R_1$ to $R_7$ independently represents any one selected from the group consisting of hydrogen, a C1 to C20 monovalent aliphatic chain group, and a C3 to C30 monovalent aliphatic ring group, wherein $L_1$ represents any one selected from the group consisting of a single bond, a substituted or unsubstituted C5 to C60 arylene group, a substituted or unsubstituted C4 to C60 heteroarylene group, and combinations thereof, wherein $Ar_1$ represents a substituted or unsubstituted C5 to C60 aryl group, wherein $P_1$ represents a substituted or unsubstituted C5 to C60 aryl group, wherein the aryl group defined as $P_1$ unsubstituted or substituted with any one selected from the group consisting of a C1 to C20 aliphatic chain linked to an aromatic ring, a C3 to C30 aliphatic ring linked to an aromatic ring, and combinations thereof,

[Chemical Formula 2]

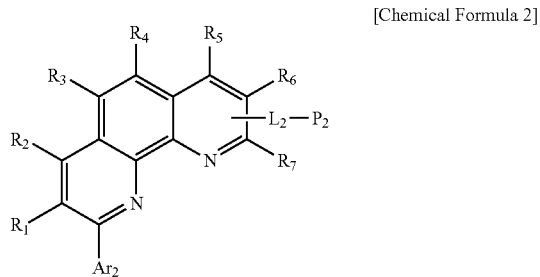

wherein, in the Chemical Formula 2, each of $R_1$ to $R_7$ independently represents any one selected from the group consisting of hydrogen, a C1 to C20 monovalent aliphatic chain group and a C3 to C30 monovalent aliphatic ring group, wherein $L_2$ represents any one selected from the group consisting of a single bond, a substituted or unsubstituted C5 to C60 arylene group, a substituted or unsubstituted C4 to C60 heteroarylene group, and combinations thereof, wherein $Ar_2$ represents a substituted or unsubstituted C5 to C60 aryl group or a substituted or unsubstituted C4 to C60 heteroaryl group, wherein $P_2$ represents a substituted or unsubstituted C4 to C60 heteroaryl group, wherein the heteroaryl group defined as $P_2$ unsubstituted or substituted with any one selected from the group consisting of a C1 to C20 aliphatic chain linked to an aromatic heterocyclic ring, a C3 to C30 aliphatic ring linked to an aromatic heterocyclic ring, and combinations thereof.

2. The organic electroluminescence device of claim 1, wherein in each of the Chemical Formula 1 and the Chemical Formula 2, each of $L_1$ and $L_2$ represents a single bond, or represents continuous bonding, at a para-position, meta-position or ortho-position, between at least two selected from a group consisting of an arylene group and a heteroaryl group.

3. The organic electroluminescence device of claim 2, wherein $L_1$ or $L_2$ represents symmetrical bonding or asymmetrical bonding between at least two selected from the group consisting of an arylene group and a heteroaryl group.

4. The organic electroluminescence device of claim 1, wherein in the Chemical Formula 2, $Ar_2$ includes a continuously bonded structure between at least two selected from the group consisting of an aryl ring and a heteroaryl ring, and wherein the aryl group defined as $Ar_2$ unsubstituted or substituted with any one selected from the group consisting of a C1 to C20 aliphatic chain connected to the continuously bonded structure, a C3 to C30 aliphatic ring connected to the continuously bonded structure, and combinations thereof.

5. The organic electroluminescence device of claim 1, wherein, in the Chemical Formula 2, $L_2$ includes a continuously bonded structure between at least two selected from the group consisting of an aryl ring and a heteroaryl ring, and wherein $L_2$ includes or does not include one selected from the group consisting of a C1 to C20 aliphatic chain connected to the continuously bonded structure, a C3 to C30 aliphatic ring connected to the continuously bonded structure, and combinations thereof.

6. The organic electroluminescence device of claim 1, wherein, in the Chemical Formula 2, $Ar_2$ includes one selected from the group consisting of a phenyl group, an alkylphenyl group, a biphenyl group, an alkylbiphenyl group, a halophenyl group, an alkoxyphenyl group, a haloalkoxyphenyl group, a cyanophenyl group, a silylphenyl group, a naphthyl group, an alkylnaphthyl group, a halonaphthyl group, a cyanonaphthyl group, a silylnaphthyl group, a phenylnaphthyl group, a pyridyl group, an alkylpyridyl group, a halopyridyl group, a cyanopyridyl group, an alkoxypyridyl group, a silylpyridyl group, a phenylpyridyl group, a pyrimidyl group, a halopyrimidyl group, a cyanopyridimyl group, a alkoxypyrimidyl group, a phenylpyrimidyl group, a quinolinyl group, an isoquinolinyl group, a phenylquinolinyl group, a quinoxalinyl group, a pyrazinyl group, a quinazolinyl group, a naphthyridinyl group, a benzothiophenyl group, a benzofuranyl group, a dibenzothiophenyl group, an arylthiazolyl group, a dibenzofuranyl group, a fluorenyl group, a carbazoyl group, an imidazolyl group, a carbolinyl group, a phenanthrenyl group, a terphenyl group, a terpyridinyl group, a phenylterpyridinyl group, a triphenylenyl group, a fluoranthenyl group, a diazafluorenyl group, and combinations thereof, wherein $Ar_2$ further has or does not have an additional substituent, wherein the additional substituent includes one selected from the group consisting of a C1 to C20 alkyl group having or free of substituting halogen, a C1 to C20 alkoxy group having or free of substituting halogen, halogen, a cyano group, a carboxy group, a carbonyl group, an amine group, a C1 to C20 alkylamine group, a nitro group, a hydrazyl group, a sulfonic acid group, a C1 to C20 alkylsilyl group, a C1 to C20 alkoxysilyl group, a C3 to C30 cycloalkylsilyl group, a C5 to C30 arylsilyl group, a C5 to C30 aryl group, a C4 to C30 heteroaryl group, and combinations thereof.

7. The organic electroluminescence device of claim 1, wherein, in the Chemical Formula 2, $L_2$ represents a single bond or includes one selected from the group consisting of a phenylene group, an alkylphenylene group, a cyanophenylene group, a naphthylene group, an alkylnaphthylene group, a biphenylene group, an alkylbiphenylene group, an anthracenylene group, a triphenylene group, a pyrenylene group, a benzothiophenylene group, a benzofuranylene group, a dibenzothiophenylene group, an arylthiazolylene group, a dibenzofuranylene group, a fluorenylene group, a triphenylenylene and combinations thereof.

8. The organic electroluminescence device of claim 1, wherein the n-type charge generation layer contains the compound represented by the Chemical Formula 1 to the compound represented by the Chemical Formula 2 in a weight ratio range of 5:95 to 95:5.

9. The organic electroluminescence device of claim 1, wherein the n-type charge generation layer further contains a dopant, wherein the dopant includes one selected from the group consisting of an alkali metal, an alkaline earth metal, an alkali metal compound, an alkaline earth metal compound, an organic complex of an alkali metal, an organic complex of an alkaline earth metal, and combinations thereof.

10. The organic electroluminescence device of claim 9, wherein the alkali metal includes any of Li, Na, K, Rb, Cs, Fr, Yb and combinations thereof,
wherein each of the alkaline earth metals and the alkaline earth metal compounds includes any one selected from the group consisting of Be, Mg, Ca, Sr, Ba, Ra, and combinations thereof,
wherein a doping concentration of the dopant is in a range from 0.5% to 10% by volume based on a total volume of the compound represented by the Chemical Formula 1 and the compound represented by the Chemical Formula 2.

11. The organic electroluminescence device of claim 1, wherein the n-type charge generation layer has a single layer structure, or a multi-layer structure including a stack of at least a first layer and a second layer, and
wherein when the n-type charge generation layer has the multi-layer structure, the first layer contains both of the compound represented by the Chemical Formula 1 and the compound represented by the Chemical Formula 2.

12. The organic electroluminescence device of claim 1, wherein the n-type charge generation layer is constructed such that the first layer is interposed between the p-type charge generation layer and the second layer, or such that the second layer is interposed between the p-type charge generation layer and the first layer.

13. The organic electroluminescence device of claim 1, wherein the at least two light-emission sub-stacks includes a first light-emission sub-stack and a second light-emission sub-stack which are sequentially stacked in this order in a direction of from the anode to the cathode,
wherein the first light-emission sub-stack further includes a first light-emission layer, and the second light-emission sub-stack includes a second light-emission layer,
wherein the first light-emission sub-stack further includes an electron transport layer, and the second light-emission sub-stack further includes a hole transport layer, such that the electron transport layer, the charge generation layer and the hole transport layer are sequentially stacked between the first light-emission layer and the second light-emission layer.

14. The organic electroluminescence device of claim 13, wherein the p-type charge generation layer contains a hole transport material or contains a hole transport material and a p-type dopant doped into the hole transport material.

15. The organic electroluminescence device of claim 14, wherein the p-type charge generation layer contains the p-type dopant,
wherein an energy gap between a lowest unoccupied molecular orbital (LUMO) level of the compound represented by the Chemical Formula 1 and a lowest unoccupied molecular orbital (LUMO) level of the compound represented by the Chemical Formula 2 satisfies Relationship 1 and Relationship 2:

[Chemical Formula 1]$_{LUMO}$-[p-type dopant]$_{LUMO}$≥
[Chemical Formula 1]$_{LUMO}$-[Chemical Formula 2]$_{LUMO}$, [Relationship 1]

[Chemical Formula 1]$_{LUMO}$-[p-type charge generation layer]$_{LUMO}$≥[Chemical Formula 1]$_{LUMO}$-[Chemical Formula 2]$_{LUMO}$, [Relationship 2]

wherein, in each of the Relationship 1 and Relationship 2,
[Chemical Formula 1]$_{LUMO}$ indicates the lowest unoccupied molecular orbital (LUMO) level of the compound represented by the Chemical Formula 1,
[Chemical Formula 2]$_{LUMO}$ indicates the lowest unoccupied molecular orbital (LUMO) level of the compound represented by the Chemical Formula 2,
[p-type dopant]$_{LUMO}$ indicates a lowest unoccupied molecular orbital (LUMO) level of the p-type dopant, and
[p-type charge generation layer]$_{LUMO}$ indicates a lowest unoccupied molecular orbital (LUMO) level of the p-type charge generation layer.

16. The organic electroluminescence device of claim 15, wherein the compound represented by the Chemical Formula 1 is selected such that the lowest unoccupied molecular orbital (LUMO) level of the compound represented by the Chemical Formula 1 is equal to or lower than a lowest unoccupied molecular orbital (LUMO) level of the electron transport layer.

17. The organic electroluminescence device of claim 15, wherein the compound represented by the Chemical Formula 2 is selected such that the lowest unoccupied molecular orbital (LUMO) level of the compound represented by the Chemical Formula 2 is equal to or higher than the lowest unoccupied molecular orbital (LUMO) level of the p-type dopant.

18. The organic electroluminescence device of claim 1, wherein the compound of Chemical Formula 1 is PA-1

PA-1

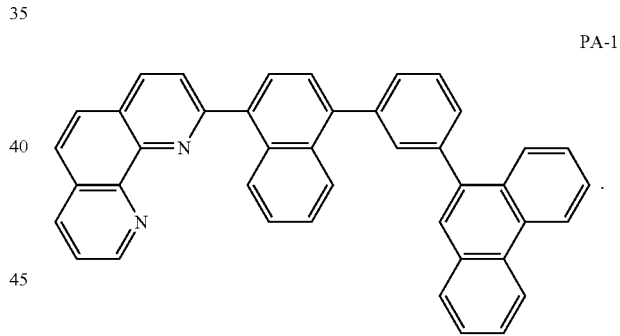

19. The organic electroluminescence device of claim 1, wherein the compound of Chemical Formula 1 is PA-2

PA-2

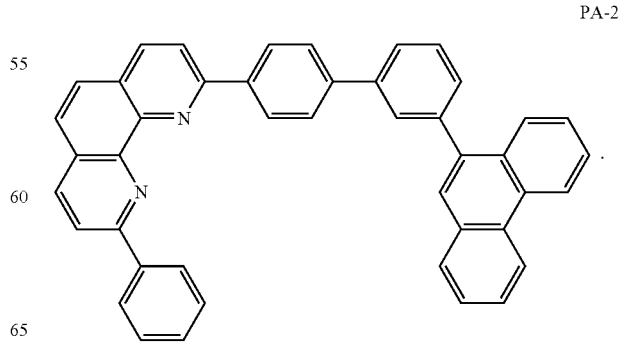

20. The organic electroluminescence device of claim 1, wherein the compound of Chemical Formula 2 is PH-1
21. The organic electroluminescence device of claim 1, wherein the compound of Chemical Formula 2 is PH-2
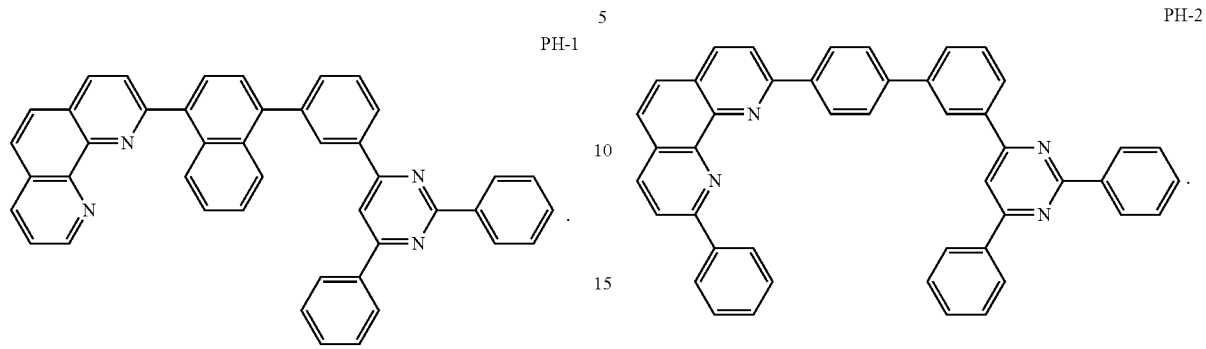
* * * * *